(12) United States Patent
Bakre

(10) Patent No.: US 8,772,455 B2
(45) Date of Patent: Jul. 8, 2014

(54) MARKERS FOR IDENTIFYING TUMOR CELLS, METHODS AND KIT THEREOF

(75) Inventor: Manjiri Bakre, Karnataka (IN)

(73) Assignee: Oncostem Diagnostics (Mauritius) Pvt. Ltd., Ebene (MU)

(*) Notice: Subject to any disclaimer, the term of this patent is extended or adjusted under 35 U.S.C. 154(b) by 0 days.

(21) Appl. No.: 13/431,919

(22) Filed: Mar. 27, 2012

(65) Prior Publication Data

US 2012/0244556 A1 Sep. 27, 2012

(30) Foreign Application Priority Data

Mar. 27, 2011 (IN) ............................ 2835/CHE/2010

(51) Int. Cl.
*C07K 14/00* (2006.01)
(52) U.S. Cl.
USPC ......................................... 530/350; 435/7.23
(58) Field of Classification Search
None
See application file for complete search history.

(56) References Cited

PUBLICATIONS

Bassarona et al Histol Histopthol 20:791-799, 2005.*
Mizuno et al, Drug Metablism and Disposition, 35:2045-2052, 2007.*
Alekwunes et al, Toxicology 250:82-88, 2008.*
Paredes et al, Breast Cancer Res 9:214, 2007.*
Hole et al, Breast Cancer Res Treat 43: 165-73, 1997, abstract.*
Al-Hajj, M. et al. "Prospective identification of tumorigenic breast cancer cells", PNAS, Apr. 1, 2003, vol. 100, No. 7, pp. 3983-3988.
Gupta, P. et al. "Identification of Selective Inhibitors of Cancer Stem Cells by High-Throughput Screening", CELL 138, Aug. 21, 2009, pp. 1-15.
Hermann PC, et al. "Cancer stem cells in solid tumors", Seminars in Cancer Biology, 2008, pp. 1-25.
Lobo, N. et al. "The Biology of Cancer Stem Cells", Annu. Rev. Cell Dev. Biol., 2007, vol. 23, pp. 675-699.
Rich, J. et al. "Chemotherapy and Cancer Stem Cells", Cell Stem Cell 1, Oct. 2007, pp. 353-355.
Sanchez-Garcia, I et al. "The theoretical basis of cancer-stem-cell-based therapeutics of cancer: can it be put into practice?", Bioessays, 2007, vol. 29, pp. 1269-1280.
Schatton, T. et al. "Identification and targeting of cancer stem cells", Bioessays, 2009, vol. 31, pp. 1038-1049.
Singh, S. et al. "Identification of human brain tumour initiating cells", Nature, Nov. 18, 2004, vol. 432, pp. 396-401.
Singh, S. et al. "Identification of a Cancer Stem Cell in Human Brain Tumors", Cancer Research, Sep. 15, 2003, vol. 63, pp. 5821-5828.

* cited by examiner

*Primary Examiner* — Lei Yao
(74) *Attorney, Agent, or Firm* — Foley & Lardner LLP

(57) ABSTRACT

The present disclosure relates to a combination of biological markers for identification of prognosis of cancer. The present disclosure further relates to a method of identifying the said markers, a method of predicting prognosis and a method of planning personalized treatment for cancer. The present disclosure further relates to a kit/test comprising the antibodies against/other methods of detecting said markers for the said prediction.

3 Claims, No Drawings

MARKERS FOR IDENTIFYING TUMOR CELLS, METHODS AND KIT THEREOF

CROSS REFERENCE TO RELATED APPLICATIONS

This application claims the benefit of the filing date of Indian Application No. 2835/CHE/2010, filed Mar. 27, 2011, the contents of which are incorporated by reference herein.

TECHNICAL FIELD

The present disclosure relates to a combination of biological markers for identification of prognosis of cancer. The present disclosure further relates to a method of identifying the said markers, a method of predicting prognosis and a method of planning personalized treatment for cancer. The present disclosure further relates to a kit/test comprising the antibodies against/other methods of detecting said markers for the said prediction.

BACKGROUND

Chemotherapy/Radiotherapy:

In the field of oncology, the detection, identification and characterization of cancer cells is an important aspect of diagnosis. Of the many challenges of medicine, none has had a more controversial beginning or has experienced more hard-fought progress than the treatment and cure of cancer. Effective treatment for most patients needed to reach every organ in the body to pin down the metastatic disease. More than 70% of cancer patients undergo chemo/radio therapy.

Despite the path breaking progress in oncology therapy from multiple angles, cancer cure still remains elusive. Advanced solid malignancies remain therapeutic challenges despite maximal therapy, in part, due to the development of resistance to radiation and chemotherapy. Eg Glioblastomas are among the most lethal of cancers with current therapies offering only palliation. Standard-of-care for glioblastoma consists of surgical resection, ionizing external beam irradiation, and chemotherapy. Radiotherapy has been the most effective nonsurgical treatment modality yet recurrence is essentially universal.

However, majority of patients undergoing chemo/radio therapy suffer from un-necessary severe side effects of the treatment. In addition many patients also show resistance to the treatment resulting in treatment failure.

Thus, there exists a need to develop diagnostic tests that can determine a priori the effectiveness of the prescribed chemo/radio therapy. Today, decisions for treatment are made on the basis of clinical parameters such as tumor histology, tumor volume as well as tumor stage and increasingly biological imaging techniques. Radiation/chemotherapy doses and schedules as well as combinations with drugs are prescribed as empirical class solutions under consideration of the tolerance limits of surrounding normal tissues. Since the current standard treatments prescriptions do not take in to account the heterogeneity/individuality of a tumor the therapies fail often and the patient undergoes un-necessary side effects.

Tumors typically have two kinds of cells, CSCs and tumor cells. CSCs constitute only a part of tumors and usually in minority. The bulk of tumor is made up of tumor cells which constantly divide and make the solid big mass called as 'tumor'.

On the other hand CSCs are quiescent cells which hardly divide and have the ability to self-renew, i.e. divide in such a way that they make a daughter cell which is a perfect copy of them-selves plus make a cells which can go and differentiate into various cells of a particular tumor (Ref: The Biology of Cancer Stem Cells, Neethan A. Lobo et al., Annu Rev. Cell Dev. Biol. 2007. 23:675-99 and The theoretical basis of cancer-stem-cell-based therapeutics of cancer: can it be put into practice?, Isidro Sanchez-Garcia et al., BioEssays 29:1269-1280)

Chemo/radiotherapies work towards curtailing tumor size by targeting and killing fast dividing cells. Since CSCs hardly divide they do not get killed by these therapies and survive to make a tumor again, which is called as 'relapse' of a cancer. (Ref: Chemotherapy and Cancer Stem Cells, Jeremy N. Rich et al., Cell Stem Cell 1, October 2007; Identification of Selective Inhibitors of Cancer Stem Cells by High-Throughput Screening, Piyush B. Gupta et al., Cell 138, 1-15, Aug. 21, 2009; Identification and targeting of cancer stem cells, Tobias Schatton et al., BioEssays 31:1038-1049; TUMOUR STEM CELLS AND DRUG RESISTANCE, Michael Dean et al., Nature Reviews, cancer, Volume 5, April 2005; Cancer stem cells in solid tumors, Patrick C. Hermann et al., *Seminars in Cancer Biology* (2008)).

From the above references it can be seen that the CSCs have been isolated from fresh tumors based on certain cell surface markers that they have, using FACS (Fluorescent Activated Cell Sorting). These isolated CSCs as few as 100-200 cells were sufficient to initiate a new tumor as against up to 10000-20000 non CSCs/bulk tumor cells. (Ref: Prospective identification of tumorigenic breast cancer cells, Muhammad Al-Hajj et al., PNAS, Apr. 1, 2003, vol. 100_no. 7_3983-3988; Identification of a Cancer Stem Cell in Human Brain Tumors, Sheila K. Singh et al., CANCER RESEARCH 63, 5821-5828, Sep. 15, 2003; Identification of human brain tumour initiating cells, Sheila K. Singh et al., NATURE | VOL 432 | 18 Nov. 2004). CSCs were identified in mid 90s in blood cancers and first time in solid tumors in 2003 from breast cancers, followed by brain and all other cancers)

Presence of CSCs and lack of drugs directed against them could be one reason cancer cure has been eluding us. Multiple pharmas and biotechs are directing their efforts to invent drugs which will specifically target these CSCs in a tumor to prevent cancer relapse etc. Many of these drugs are in clinical trials.

The resistance to chemo/radio therapy and the treatment failure is due to presence of what are called Cancer Stem Cells (CSC) in the tumor. Tumors are heterogeneous in nature and contain 2 kinds of cells, cancer stem cells and tumor cells which form the bulk of the tumor. While it has been recognized for a long time that not all tumor cells have the potential to initiate a new tumor, or a recurrence after treatment, only recently methodological advances have emerged that eventually allowed identification of CSCs and to investigate their biology. CSCs have been prospectively isolated from a growing number of human cancers, including leukemias and tumors of the breast, brain, colon, head & neck and pancreas. For different tumors it has been shown that transplantation of CSC subpopulations led to higher tumor take rates when compared to unsorted populations from the same tumor.

A CSC is defined as a cell within the tumor that possesses the capacity to self-renew and to generate the heterogeneous lineages of all cancer cells that comprise a tumor. This implies that CSCs are possibly a small subpopulation of tumor cells which are able to expand the CSC pool or differentiate into cancer progenitor cells by symmetric or asymmetric division. However, this point is tumor dependent and in melanomas CSCs contributed to a significantly higher percentage of total tumor cells. The non-stem cells constitute the bulk of all cancer cells within the tumor, but have only limited proliferative potential and are non-tumorigenic.

Properties of CSCs:

CSCs are quiescent cells present in the tumor and thus are functionally different from the rapidly proliferating tumor cells which make up the bulk of the tumor. CSCs by virtue of being quiescent in nature are able to resist the 'desirable effects' chemo/radio therapy well as these therapies target the rapidly dividing cells of the tumor. In addition CSCs are endowed with multiple ion channels/transports, higher hypoxia tolerance and differential gene expression, etc. which contribute to their chemo/radio resistance phenomenon. An increasing body of data suggests biological differences of CSCs and non-CSCs are crucial to respond to the standard therapies and most pharmas are using these differences to design rational drugs against CSCs. For failure of radiotherapy and chemotherapy treatments, one underlying reason might be a low efficacy of current treatments on eradication of cancer stem cells (CSCs). Growing evidence indicating that CSCs are resistant to cytotoxic/radiation therapies and may thus contribute to treatment failure.

The current technologies that exist in the field similar to the instant disclosure include Oncotype Dx, and Mammaprint. These are similar but they do not detect presence of CSCs. They assess presence of ER/PR and Her-2-neu pathways in patients to assess if a patient needs post-operative chemotherapy. Currently there are no diagnostic tests which detect presence of CSCs in tumors and hence cannot predict relapse time and usefulness of chemo and radiotherapy. In addition, current methods do not offer help in choosing a particular chemotherapy drug/combination.

From a clinical point of view, the direct consequence of this concept is that cancer therapy can cure a patient only if all CSCs are eliminated and that a single surviving CSC can cause a recurrence or metastasis. In addition it also implies that if the tumor is assessed for presence of CSCs before prescribing the chemo/radio therapy there is a fair chance that the oncologist can predict the effectiveness of the treatment, manage the cancer treatment better and reduce the unwanted side effects of the treatment to patients in cases when the therapy is ineffective. Since the discovery of first solid tumor CSCs in 2004 there have been great advances in CSC biology. Predictive tests for content, distribution and sensitivity of CSCs, microenvironmental CSC niches and signatures should be used to allow CSC-based individualized tailoring of therapy within the class solutions.

BRIEF SUMMARY OF THE DISCLOSURE

Accordingly, the present disclosure relates to biological marker selected from a group comprising CD44, CD24, ABCG2, ESA, ABCC4, CD133, Oct-4, Sox-2, APC, β-catenin and P-cadherin or any combination thereof for prognosis of cancer; a kit for prognosis of a subject having cancer or suspected of having cancer, said kit comprising antibody against biological marker selected from a group comprising CD44, CD24, ABCG2, ESA, ABCC4, CD133, Oct-4, Sox-2, APC, β-catenin and P-cadherin or any combination thereof, optionally along with organic solvent, reagent, secondary antibody, enzyme for performing immunohistochemistry and instruction manual; a method of identifying biological marker on cells in a biological sample being or suspected of being a tumor, said method comprising acts of a) collecting, fixing, sectioning and treating the biological sample with organic solvent, followed by antigen retrieval using predetermined sample dilutions and b) adding primary antibody against biological marker selected from a group comprising CD44, CD24, ABCG2, ESA, ABCC4, CD133, Oct-4, Sox-2, APC, β-catenin and P-cadherin or any combination thereof and adding secondary antibody conjugated with an enzyme and reagents for obtaining a colored reaction or fluorescence for identifying the biological marker; a method of prognosis of a subject having cancer or suspected of having cancer, said method comprising acts of a) collecting biological sample from the subject and identifying expression or absence of receptors selected from a group comprising estrogen receptor, progesterone receptor and Her-2-neu receptor or any combination thereof in cells of the sample to obtain expression identified cells, b) carrying out immunohistochemistry analysis on the cells of step (a) with antibody against biological marker selected from a group comprising CD44, CD24, ABCG2, ESA, ABCC4, CD133, Oct-4, Sox-2, APC, β-catenin and P-cadherin or any combination thereof and c) identifying expression or absence of the receptors and the one or more biological markers in cells of the sample and correlating the identification of the marker with predictive outcome reference table for predicting the prognosis of the subject; and a method of treating cancer, said method comprising acts of a) identifying biological marker selected from a group comprising CD44, CD24, ABCG2, ESA, ABCC4, CD133, Oct-4, Sox-2, APC, β-catenin and P-cadherin or any combination thereof, on tumor cells in a biological sample and predicting prognosis of a subject having cancer or suspected of having cancer and b) based on the prediction, designing a cancer therapy for suppression of the cancer.

DETAILED DESCRIPTION OF THE DISCLOSURE

The present disclosure relates to, biological marker selected from a group comprising CD44, CD24, ABCG2, ESA, ABCC4, CD133, Oct-4, Sox-2, APC, β-catenin and P-cadherin or any combination thereof for prognosis of cancer.

In an embodiment of the present disclosure, the cancer is breast cancer.

In another embodiment of the present disclosure, the marker is located on tumor cells of the cancer at locations selected from a group comprising cell membrane, cytoplasm, nucleus, and nuclear membrane or any combination thereof.

The present disclosure, further relates to a kit for prognosis of a subject having cancer or suspected of having cancer, said kit comprising antibody against biological marker selected from a group comprising CD44, CD24, ABCG2, ESA, ABCC4, CD133, Oct-4, Sox-2, APC, β-catenin and P-cadherin or any combination thereof, optionally along with organic solvent, reagent, secondary antibody, enzyme for performing immunohistochemistry and instruction manual.

The present disclosure, further relates to a method of identifying biological marker on cells in a biological sample being or suspected of being a tumor, said method comprising acts of:

a) collecting, fixing, sectioning and treating the biological sample with organic solvent, followed by antigen retrieval using predetermined sample dilutions and adding primary antibody against biological marker selected from a group comprising CD44, CD24, ABCG2, ESA, ABCC4, CD133, Oct-4, Sox-2, APC, β-catenin and P-cadherin or any combination thereof; and b) adding secondary antibody conjugated with an enzyme and reagents for obtaining a colored reaction or fluorescence for identifying the biological marker.

In an embodiment of the present disclosure, the cancer is breast cancer.

In another embodiment of the present disclosure, the organic solvent is selected from a group comprising alcohol and xylene or any combination thereof.

In yet another embodiment of the present disclosure, the collecting, fixing, sectioning and treating is carried out under predetermined conditions by conventional immunohistochemistry technique.

The present disclosure further relates to a method of prognosis of a subject having cancer or suspected of having cancer, said method comprising acts of:
a) collecting biological sample from the subject and identifying expression or absence of receptors selected from a group comprising estrogen receptor, progesterone receptor and Her-2-neu receptor or any combination thereof in cells of the sample to obtain expression identified cells;
b) carrying out immunohistochemistry analysis on the cells of step (a) with antibody against biological marker selected from a group comprising CD44, CD24, ABCG2, ESA, ABCC4, CD133, Oct-4, Sox-2, APC, β-catenin and P-cadherin or any combination thereof; and
c) identifying expression or absence of the receptors and the one or more biological markers in cells of the sample and correlating the identification of the marker with predictive outcome reference table for predicting the prognosis of the subject.

In an embodiment of the present disclosure, the immunohistochemistry analysis is carried out by conventional method and wherein the identification of markers is carried out by visualizing a colored reaction or fluorescence obtained at completion of the method due to staining of the cells from the sample.

In another embodiment of the present disclosure, the correlating is based on parameters selected from a group comprising percentage of staining, intensity of staining and location of staining or any combination thereof; and wherein the location of the staining is selected from a group comprising cell membrane, cytoplasm, nucleus, and nuclear membrane or any combination thereof.

In yet another embodiment of the present disclosure, the correlating comprises multiplying the percentage of staining with the intensity of staining to arrive at a predictive score in order to predict the prognosis as being good or bad depending on the location of expression of the biological marker.

In still another embodiment of the present disclosure, the predictive score is selected from a group comprising low score ranging from about 1 to about 80, moderate score ranging from about 81 to about 150 and high score ranging from about 150 to about 300.

In still another embodiment of the present disclosure, the predictive outcome reference table is individually or a combination of tables selected from a group comprising 1, 1A, 2, 2A, 3, 3A, 4, 4A, 5, 6, 6A, 7, 7A, 8, 9 and 10 or any combination of tables thereof.

The present disclosure further relates to a method of treating cancer, said method comprising acts of:
a) identifying biological marker selected from a group comprising CD44, CD24, ABCG2, ESA, ABCC4, CD133, Oct-4, Sox-2, APC, β-catenin and P-cadherin or any combination thereof, on tumor cells in a biological sample and predicting prognosis of a subject having cancer or suspected of having cancer; and
b) based on the prediction, designing a cancer therapy for suppression of the cancer.

The present disclosure is a diagnostic test that assesses the tumor sample using certain CSC specific markers using immunohistochemistry and reverse transcription polymerase reaction (RT-PCR) as a technique to find out the presence of CSCs/drug resistant cells in the given tumor which are indicative of the response of the patient to standard therapies. Examples of markers which includes but is not limited to by the following markers: CD44, CD133, CD24, Oct 4, Sox2, and ion transporters/channels present on CSCs such as the ABC family of transporters namely ABCG2 and ABCC4, ESA, APC, P-cadherin, B-catenin (phospho, total and unphospho).

The present disclosure has utility in the field of oncology for the early detection of tumors. The diagnosis/prognosis of a possible cancer will help oncologist in planning the chemo and prescribing alternate targeted treatment. The patient will be further spared from unwanted side effects of the expensive treatment.

The present disclosure also relates to markers used to identify the CSCs and a combination of these markers and methodologies to detect such Cancer Stem Cells (CSCs).

A more complete understanding can be obtained by reference to the following specific examples, which are provided for purposes of illustration only and are not intended to limit the scope of the disclosure.

The following examples represent various markers which may be used either individually or in combination with each other for prognosis of breast cancer. The examples provided herein illustrate the kinds of combinations which are possible for analysing and arriving at prognosis of a subject having or suspected of having cancer. The tables provided herein are combined for the sake of representation and clarity as to how to arrive at an interpretation by perceiving either a combination of markers or the markers individually. Any table from any combination illustrated herein may be used either single or in combination with any other marker provided herein for an interpretation which may not have been explicitly illustrated by way of the examples herein. All such possible combinations and interpretations of such combinations fall within the scope of the instant disclosure. A person skilled in the art would therefore be able to envisage the prognosis of a subject by way of examining the sample, arriving at results, and comparing the results with the interpretation of the markers provided herein, for accurate prognosis and strategize the course of further treatment based on such prognosis.

EXAMPLES

In the present disclosure, IHC (immunohistochemistry) is performed with two antibodies against CD44 and CD24 to understand if any CSC signature in these patients can be seen. The signature being looked for is $CD44^{+}/CD24^{-/low}$ However, these two markers are known to be present on CSCs based on FACS analysis, which only detects surface/membrane associated expression. FACS can only detect membrane expression, so even though CD24 expression is seen in cytoplasm in many cases, it is considered as negative or it is marked as cytoplasmic. However, IHC can detect presence of CD24 in both membrane and cytoplasm and in many cases expression can be seen in the cytoplasm in addition to membrane or at times in cytoplasm only. Therefore, in cases where the expression is entirely cytoplasmic as disclosed in some of the tables of the instant disclosure, the results in them can be considered as CD24− (CD24 negative) if detected using FACS, unlike using IHC in the instant disclosure. Because of detection based on IHC in the instant disclosure, membrane as well as cytoplasmic, and nuclear membrane expression is detected.

In an embodiment of the present disclosure, it is to be noted that cancer/tumour node status/stage N0 also at times reflects bad outcome. However, as common practice, usually increase in node stage Eg: N2 or N1 reflect bad outcome, whereas N0 is considered to have no metastasis to the adjoining nodes and thus resulting in good outcome/having less severe form of cancer/tumor. Nonetheless, table 10 (patient history) disclosed in the instant disclosure clearly depicts that there are bad outcomes with lower node stage tumors and vice versa as well. Hence, the node status cannot be completely relied upon and thus a deeper analysis of the sample is required since good or bad prognosis cannot be solely carried out based on such priorly known techniques, as node status identification. Therefore, the instant disclosure clearly reflects that need and importance of identification of markers present on cancer cells which may be combined with previously known techniques such as the tumor node status. Thus, as is apparent from the instant disclosure, a combination of the % of cells stained, intensity of staining and location of the respective markers is to be considered for arriving at the correct prognosis of a patient sample.

In another embodiment of the present disclosure, it is also to be noted that the markers reflected below are to be identified, not only in the cancer stem cells/cancer initiating cells/tumor initiating cells of the patient sample, but instead also to encompass all the tumor cells of the sample.

Example 1

The technique used for the identification of markers in a patient sample in the present disclosure involves Immunohistochemistry (IHC) or RT-PCR.

The process of identifying the Cancer Stem Cells from the tumor is carried out using the technique as below:

Tumor sample is collected from the patient. The sample is formalin fixed by embedding the sample in paraffin to make a block
↓
The block is sectioned on a slide
↓
The slide is passed through a series or organic solvents to dehydrate the water
↓
Antigen retrieval is carried out under controlled experimental conditions, using specific sample dilutions
↓
This is followed by cooling the section on the slide to room temperature (RT)
↓
Followed by adding blocking agent
↓
Followed by adding of primary antibody against the antigen
↓

-continued
Followed by adding of secondary antibody conjugated with an enzyme
↓
Followed by adding of reagents for obtaining a coloured reaction
↓
Oberserving staining for identification of % of staining, intensity and location of staining. Correlating all these results to arrive at a conclusion for identifying presence of CSC's in the tumour sample and arriving at a resulting good/bad outcome.

In an embodiment of the present disclosure, the organic solvents, reagents, secondary antibody and enzymes mentioned in the detailed protocol below are only for the purposes of illustration and should not be construed to be limiting in nature. The instant disclosure envisages and encompasses all possible combinations and alternatives of such solvents, reagents, secondary antibody and enzymes known and commonly used by a person skilled in the art.

To further provide clarity on the process employed in the present disclosure, the detailed protocol of the immunohistochemistry is provided as below:

IHC Protocol

A] Coating Slides and Cutting a Section of FFPE Block:
1. Wash new glass slides with tap water.
2. Dip the slides with 1% acid alcohol solution (1 ml HCl+99 ml of 70% ethanol) for 5 mins.
3. Wash the slides with distilled water once to make sure the acid alcohol is washed off.
4. Dry the slides.
5. Dip the slides in 10% Poly-L-lysine solution (PLL) in water for 15 minutes at room temperature (RT).
6. Remove the slides and dry them at RT.
7. Take a 3-5 micron section of the FFPE tumor block on these PLL coated slides using Leica Microteome.
8. Incubate the section at 60C for 3 hrs or over night.

B] De-Paraffinization Protocol:
1. Dip the slides with tumor section in Xylene-I for 10 mins at RT.
2. Dip the slides in Xylene-II for 10 mins at RT.
3. Dip the slides in Xylene-III for 10 mins at RT.
4. Dip the slides in 100% alcohol for 5 mins at RT.
5. Dip the slides in 100% alcohol for 5 mins at RT.
6. Dip the slides in 70% alcohol for 5 mins at RT.
7. Dip the slides in 70% alcohol for 5 mins at RT.
8. Dip the slides in D/W for 5 mins at RT.
9. Dip the slides in 3% H2O2 in methanol at RT for 20-30 mins.

C] Antigen Retrieval and Immunostaining:
This step will be different for each antibody/marker. Following the protocol for antibody A and B. The buffer for antigen retrieval for both antibodies is as follows: 1 mM EDTA+10 mM Tris-Cl buffer at pH 7.4
1. For antibody A: The antigen is best retrieved by using pressure cooker conditions in Tris-EDTA buffer 3 whistles (depending on your pressure cooker, the number whistles can be adjusted. Please avoid over cooking).

For antibody B: The antigen is best retrieved by using microwave conditions as follows:
800 Watts for 6 mins
800 watts for 6 mins
200 watts for 15 mins
However, one can also try pressure cooker method as above.

2. After the antigen retrieval, cool the slides to RT in the buffer itself for 30 mins.
3. Wash the slides in distilled water for 2 mins.
4. Wash the slides in TBST (Tris-Buffered Saline with 0.1% Tween 20) for 5 mins.
5. Wash the slides in TBST for 5 mins.
6. Block the slides with 3% BSA solution/if you are using a kit for the secondary antibody then use the blocking given by the kit as appropriate.
7. Add primary antibody diluted in buffer (see below) for 60 mins at RT.
8. Wash the slides in TBST for 5 mins at RT.
9. Repeat step #8 twice more.
10. Add secondary antibody i.e. HRP conjugated anti-mouse antibody at the appropriate dilution as per kit. Incubate at RT for 30-60 mins.
11. Wash in TBST for 5 mins at RT.
12. Repeat step #11 twice more.
13. Add the substrate DAB etc. as per the recommendation by the kit.
14. Wash off the excess substrate as per kit.
15. Counter stain with haematoxylin.
16. Wash off excess stain by dipping in 100% alcohol for 5 mins.
17. Repeat step #16.
18. Dry the slides.
19. Wash in xylene once for 5 mins at RT.
20. Mount in DPX/appropriate mounting medium.
21. Score/grade the slides as per the sheet.

Recipes for solutions:
1. Acid alcohol: 1 ml of conc HCl+99 ml of 70% alcohol.
2. Antigen retrieval buffer: 10 mMEDTA pH 8.0+10 mM Tris-Cl pH 7.4.
3. Primary Antibody dilution buffer: 10 mM Tris-Cl pH7.4+0.9% NaCl+0.5% BSA.
4. Blocking buffer: 3-5% BSA in Tris-Cl pH 7.4 OR use blocking solution given by the kit OR as per your protocol.
5. TBST: 10 mM Tris-Cl pH 7.4+0.9% NaCl+0.1% Tween-20.

Further, the specific sample dilutions, organic solvents and experimental conditions employed for antigen retrieval are provided as below, only for the purposes of illustration. A person skilled in the art would be able to comprehend the various parameters and conditions that are employed and thus all the various alternatives and substitutes known to the person having skill in the art for arriving at a protocol for such analysis are also under the purview of the instant disclosure:

Antibody A—Pressure cooker (PC), Tris-EDTA (TE) pH 7.4 buffer, 2 whistles at setting 2 and 1 whistle at setting 1 (Steamed for 20 mins at about Temp. 100° C.+10 mins at 121° C. at pressure about 10 psi); 1:1400 dilution.

Antibody B—Microwave, 50 mM Citrate buffer pH 6.0; Microwave/Cit 6.0/7 min at 'high' setting-700 W; 5 min at High-750 W; 15 min at 'defrost' setting-200 W; Dilution 1:50.

Antibody C—2N HCl, RT; 1:300 dilution.

Antibody E—Water bath at 90C for 30 mins in 50 mM Citrate buffer pH 6.0; Dilution 1:600.

Antibody F—Pressure Cooker, Citrate buffer pH-6; 1 whistle at 1 setting on the heater and boil 20 mins at 1 setting (Steamed for: 40 mins at about 100° C. pressure+10 mins at about 10 psi at 121° C.); Dilution 1:200.

Antibody G—2N HCl, RT 15 minutes, 1:50 dilution.

Antibody H—PC/Cit 6.0/2 whistles at 2 setting & 1 whistle at 1 setting; Dilution 1:1000.

Antibody I—Pressure cooker (2 whistles at 2 minutes, 1 whistle at 1 setting), Cit 6.0; Dilution 1:1000.

Antibody J—Pressure Cooker, Cit 6.0—Pressure cooker (2 whistles at 2 minutes, 1 whistle at 1 setting); Antibody dilutions of 1:50.

Antibody K—Water bath at 90C for 30 minutes in Citrate, pH 6.0; 1:100 dilutions.

Antibody L—Pressure cooker (2 whistles at 2 minutes, 1 whistle at 1 minute), TE buffer at 7.4 pH, prediluted antibody from company.

Antibody O—Pressure cooker in Citrate buffer pH 6.0 at 2 whistles at 2 setting and 1 whistle at 1 setting.

Example 2

The antibodies being used in the instant disclosure are selected from one or more of the following:

CD44: (Ref: CD44 Std./HCAM Ab-4 (Clone 156-3C11))
CD24: (Ref: (CD24 (GPI-linked surface mucin) Ab-2 (Clone SN3b)
ABCG2: (Ref: NB-11093511 from Novus Biologicals)
ESA: (Ref: Novocastra Epithelial Specific Antigen)
ABCC4: (Ref: ABCC4 monoclonal antibody (M03), clone 1B2)
CD133: (Ref: PAB-12663 from Abnova)
Oct-4: (Ref: OCT4 Antibody (NB110-90606))
Sox-2: (E-18600 from Spring Biosciences)
APC: (Ref: Adenomateous Polyposis Coli gene product)
P-cadherin: (Ref: Anti-P cadherin antibody [56C1], prediluted (ab75442))
B-catenin: (Ref: Anti-Active-β-Catenin (anti-ABC), clone 8E7) JBC-1870057.

In all the tables below from tables 1-9, the intensity of cells stained, have the values ranging from 1 to 3. Here, intensity 1=very light brown colour of slide stained, intensity 2=medium brown colour of slide stained and intensity 3=dark brown colour of slide stained. Intermediate colour observation is referred as 1-2 or 2-3 etc.

Further, the tables provided herein selected from a group comprising table 1, 1A, 2, 2A, 3, 3A, 4, 4A, 5, 6, 6A, 7, 7A, 8, 9 and 10, either individually or any combination of tables thereof may be used by a person skilled in the art to interpret and arrive at relevant results for prediction of prognosis for a subject having or suspected of having cancer. These tables individually or in combination may also be referred to as predictive outcome reference table in the instant disclosure.

TABLE 1

| Serial No of Patients | Antibody A CD44 | | | Antibody B CD24 | | |
|---|---|---|---|---|---|---|
| | % of cells | intensity | location | % of cells | intensity | location |
| ER+/PR+ GOOD OUTCOME | 1 | 20 | 1-2 | M | 60 | 1.5 | M |
| | | | | | 80 | 1.5 | C |
| | 2 | 20 | 2-3 | M | 10 | 1.5 | M |
| | | | | | 40 | 1.5 | C |

TABLE 1-continued

|  | Serial No of Patients | Antibody A CD44 | | | Antibody B CD24 | | |
|---|---|---|---|---|---|---|---|
|  |  | % of cells | intensity | location | % of cells | intensity | location |
|  | 3 |  | Negative |  | 55 | 1.5 | C |
|  | 4 | 35 | 2 | M | 65-70 | 1.5 | C |
|  | 5 | 5 | 3 | M | 85 | 3 | M |
|  |  |  |  |  | 50 | 2 | C |
|  | 6 | 40 | 2-3 | M | 80 | 2-3 | C |
|  |  |  |  |  | 20 | 1-2 | M |
|  | 7 | 40 | 3 | M | 35-40 | 3 | C |
|  |  |  |  |  | 25-30 | 2 | M |
|  | 8 | 10 | 1.5 | C | 75 | 2 | C |
|  |  |  |  |  | 35-40 | 1.5 | M |
|  | 9 | 20 | 3 | M | 25 | 1.5 EACH | M |
|  |  |  |  |  | 15 |  | C |
| ER+/PR+ | 10 | 20 | 1.5 | M | 95 | 1.5 | C |
| BAD |  | 60 | 2 | C |  |  |  |
| OUTCOME | 11 | 95 | 3 | M | <10 | 1 | M |
|  |  |  |  |  | 90 | 1 | C |
|  | 12 | 70 | 3 | M | 50 | 2-3 | M |
|  |  |  |  |  | 70 | 1-2 | C |
|  | 13 | 90 | 2.5 | M | 95 | 2.5 | C |
|  | 14 | 75 | 1.5 | M | 95 | 1.5 | C |
|  |  |  |  |  | 80 | 1.5 | M |
|  | 15 | 60 | 2.5 | M | 70 | 1.5 | C |
|  | 16 | 80-85 | 3 | M | 10 | 1.5 | C |
|  |  |  |  |  | 20 | 2 | M |
|  | 17 | 65-70 | 3 | M | 55 | 1.5 | C |
|  | 18 | 90 | 3 | M | 50 | 1 | M |
|  |  |  |  |  | 50 | 1 | C |
| ER−/PR− | 19 | 100 | 2-3 | M | 70 | 1 | M |
| GOOD |  |  |  |  | 70 | 1 | C |
| OUTCOME | 20 | 90 | 3 | M | 50 | 1-2 | M |
|  |  |  |  |  | 70 | 3 | C |
|  | 21 | 80 | 3 | M | 60 | 1-2 | M |
|  |  |  |  |  | 70 | 1 | C |
|  | 22 | 40 | 2.5 | M | 95 | 1.5 | C |
|  |  |  |  |  | 60 | 1.5 | M |
|  | 23 | 95 | 3 | M | 60 | 2-3 | M |
|  |  |  |  |  | 90 | 2-3 | C |
|  | 24 | 95 | 3 | M | 50 | 1.5 | C |
|  |  |  |  |  | 20 | 1.5 | M |
|  | 25 | 90 | 3 | M |  | Negative |  |
|  | 26 | 95 | 3 | M | 10 | 1.5 | M |
|  | 27 | 80 | 3 | M | 45 | 1.5 | C |
|  |  |  |  |  | 35 | 1.5 | M |
| ER−/PR− | 28 | <5 | 1 | M | 60-70 | 1-2 | M |
| BAD |  |  |  |  | 40 | 1-2 | C |
| OUTCOME | 29 | 75 | 3 | M | 20 | 1-2 | C |
|  |  | 20 | EACH | C |  |  |  |
|  | 30 | 5 | 1-2 | M | 50 | 2-3 | M |
|  |  |  |  |  | 90 | 2-3 | C |
|  | 31 | 30 | 2.5 | M | 40 | 2-3 | M |
|  |  | 50 | 2 | C | 60 | 2-3 | C |
|  | 32 | 70 | 1.5 | M | 95 | 2.5 | C |
|  |  | 40 | 1.5 | C | 55 | 1.5 | M |
|  | 33 | 60 | 2.5 | M | 95 | 2 | C |
|  |  | 40 | 1.5 | C | 50 | 2 | M |
|  | 34 | 45 | 2.5 | M | 90 | 1.5 | C |
|  |  | 30 | 1.5 | C | 45 | 1.5 | M |
|  | 35 | 30 | 2.5 | M |  | Negative |  |
|  | 36 | 35 | 3 | M | 50 | 2 | C |
|  |  | 15 | 1-2 | C | 30 | 1.5 | M |

TABLE 1A

| ER/PR Status | Outcome | Expression level and location | | Potential use |
|---|---|---|---|---|
|  |  | Marker A | Marker B |  |
| P/P | Good | Low expression in M 65 | Moderately high when expression in C alone 91.5 | Less aggressive follow-up |

TABLE 1A-continued

| ER/PR Status | Outcome | Marker A | Marker B | Potential use |
|---|---|---|---|---|
| | | | Expression level and location | |
| | | | When expressed in MC, C is higher than M<br>M-65<br>C-108 | |
| | Bad | High expression in M<br>213 | Moderate when expression in C alone<br>142<br>When expressed in MC, C is higher than M<br>M-57<br>C-82 | More aggressive treatment |
| N/N | Good | High expression in M<br>238 | When expressed in MC, C is higher than M<br>M-82<br>C-119 | Less aggressive treatment |
| | Bad | Low when expression in M alone<br>20<br>When expressed in MC, M is much higher than C<br>M-131<br>C-58.5 | When expressed in MC, C is much higher than M<br>M-91<br>C-148 | Clues for better follow-up |

Expression of A/CD44 should be scored at the invasive edge and not at DCIS edge
M: cell membrane
C: cytoplasm
N: nucleus
NM: Nuclear membrane
Ranges:
Low: 1-80;
Moderate: 81-150;
High 150-onwards Formula Applied for Scoring:

Total of Column A (% of cells)/number of patient samples=score A Total of Column B (intensity)/number of patient samples=score B Score A multiplied by Score B=Final score for that Marker in that category. The above scoring and formula has been used keeping in mind the entities only in a specific field [location of the marker] and not across all the patient samples of that category. For Example: in ER−/PR− status of patients with bad outcome for Marker A, the scoring for predicting the prognosis is carried out in the following manner:

For arriving at an interpretation of expression of Marker A in Membrane and Cytoplasm together, only 6 out of the 9 samples are considered, as the remaining 3, constitutes samples having expression only in the Membrane.

Similarly, for arriving at an interpretation of expression of Marker A in Membrane alone, only 3 out of the 9 samples are considered, as the remaining 6, constitutes samples having expression both in Cytoplasm and Membrane, and not in Membrane alone, which is the required criteria for the prediction in this category.

Similar strategy and conversion is employed for interpreting results of all the samples, across all the markers and ER/PR status.

Note: ER+/PR+ Good Outcome:

It is critical to assess the presence or absence of marker A at invasive edge. It is possible that the entire tumor with DCIS focus has HIGH expression of A but the invasive edge has low or no expression and therefore, it is the actual expression at the invasive edge that is very important for the interpretation of results for Marker A.

Table 1 and 1A Interpretation:

Patient sample is segregated based on ER+/PR+ status as one group and ER−/PR− status as another group. On selection and segregation of such expression, the test sample is checked for the presence of either individual markers or a combination of markers (for example as captured here: CD44 in combination with CD24 is taken into account) mentioned in Table 1.

The result for good and bad prognosis/outcome should ideally show the marker status after taking into account the expression of staining intensity in conjunction with location of the marker and % of staining as disclosed in Table 1.

A pattern of good/bad outcome as depicted in Table 1A can be arrived at, by correlating the 3 entities namely % of staining, staining intensity and location of the marker in the sample after carrying out the process steps disclosed as aforementioned under Example 1. It is to be noted that it is critical to assess the presence or absence of marker A at invasive edge. It is possible that the entire tumor with DCIS focus has HIGH expression of A but the invasive edge has low or no expression and therefore, this aspect is very important for the interpretation of results for Marker A.

If the results obtained after conducting the aforementioned process steps on the test sample coincide with the marker expression results for good outcome (as disclosed in Table 1), the treatment module followed for the patients having good outcome as per Table 10 (patient history) can be referred to and treatment strategy for such patients will therefore require lesser follow up or less aggressive treatment strategy. However, in case of sample results coinciding with marker expression results for bad outcome (as disclosed in Table 1), then such patients will require more aggressive follow ups along with strategic treatment module to be followed OR an alternate treatment approach needs to be employed or conceived which can essentially comprise developing and administering antibodies specific to these combination of markers (here CD44 and CD24) to curtail its expression Increasingly the world over it has been realised that there is a subset of patients in ER+/PR+ group who tend to have bad outcome. Our above mentioned results can segregate ER+/PR+ women with potential good and bad outcome based on expression of CD44 and CD24. However, a person skilled in the art would be able to comprehend that based on the above mentioned results, one way to treat these patients is to prescribe anti-CD44 antibodies since CD44 is highly expressed in the cell-membrane in these patients with a hope of long term disease free survival. On the other hand, in ER−/PR− patients with potential bad outcome, there is low over all expression of CD44, and so antibodies to CD44 will not help much. Nevertheless, it is important to identify them and treat them appropriately with more targeted drugs, frequent and thorough follow-ups etc. to ensure long term disease free survival. Similar strategy can be employed for treating cancer patients with varied marker expressions, some of which are illustrated in the tables below.

It is also to be noted that Good outcome from across ER/PR status cannot be combined. As aforementioned, typically +/+ patients are considered good prognosis cases and hence are need not be treated aggressively. Typically, follow ups for +/+ patients can be carried out every 6-12 months which can be too long for the +/+ bad outcome group. Thus, with the aforementioned interpretation of outcome, it can be inferred that there can be more frequent follow-ups to reduce cancer recurrences between two follow-ups, called interval recurrences, especially for the +/+ bad outcome cases/patients. On the other hand −/− cancers are aggressive cancers and hence patients with good outcome need not be aggressively treated. Whereas, −/− patients with bad outcomes, can have more detailed, effective and innovative follow-ups to catch the metastasis as early as possible and start the treatment.

TABLE 2

|  | Serial No of Patients | Antibody A CD44 | | | Antibody B CD24 | | | Antibody F ABCC4 | | |
|---|---|---|---|---|---|---|---|---|---|---|
|  |  | % of cells | intensity | location | % of cells | intensity | location | % of cells | intensity | location |
| ER+/PR+ GOOD OUTCOME | 1 | 20 | 1-2 | M | 60 | 1.5 | M | 20 | 1-2 | M |
|  |  |  |  |  | 80 | 1.5 | C |  |  |  |
|  | 2 | 20 | 2-3 | M | 10 | 1.5 | M | 30 | 1.5 | M |
|  |  |  |  |  | 40 | 1.5 | C |  |  |  |
|  | 3 |  | Negative |  | 55 | 1.5 | C |  | Negative |  |
|  | 4 | 35 | 2 | M | 65-70 | 1.5 | C | 60 | 1.5 | C |
|  |  |  |  |  |  |  |  | 35 | EACH | M |
|  | 5 | 5 | 3 | M | 85 | 3 | M | 50 | 2 | M |
|  |  |  |  |  | 50 | 2 | C |  |  |  |
|  | 6 | 40 | 2-3 | M | 80 | 2-3 | C | 20 | 2 | M |
|  |  |  |  |  | 20 | 1-2 | M | 20 | 2 | C |
|  | 7 | 40 | 3 | M | 35-40 | 3 | C | 20 | 2 | M |
|  |  |  |  |  | 25-30 | 2 | M | 30 | 2 | C |
|  | 8 | 10 | 1.5 | C | 75 | 2 | C | 50 each | 1-2 | C |
|  |  |  |  |  | 35-40 | 1.5 | M |  | 1-2 | M |
|  | 9 | 20 | 3 | M | 25 | 1.5 EACH | M | 15 | 1.5 | M |
|  |  |  |  |  | 15 |  | C | 15 |  |  |
| ER+/PR+ BAD OUTCOME | 10 | 20 | 1.5 | M | 95 | 1.5 | C | 50 | 1.5 | C |
|  |  | 60 | 2 | C |  |  |  |  |  |  |
|  | 11 | 95 | 3 | M | <10 | 1 | M |  | Negative |  |
|  |  |  |  |  | 90 | 1 | C |  |  |  |
|  | 12 | 70 | 3 | M | 50 | 2-3 | M | 70 | 2 | M |
|  |  |  |  |  | 70 | 1-2 | C |  |  |  |
|  | 13 | 90 | 2.5 | M | 95 | 2.5 | C | 90 | 3 | C |
|  |  |  |  |  |  |  |  | 50 | 2 | M |
|  | 14 | 75 | 1.5 | M | 95 | 1.5 | C | 80 | 1.5 | M |
|  |  |  |  |  | 80 | 1.5 | M |  |  |  |
|  | 15 | 60 | 2.5 | M | 70 | 1.5 | C |  | Negative |  |
|  | 16 | 80-85 | 3 | M | 10 | 1.5 | C |  | Negative |  |
|  |  |  |  |  | 20 | 2 | M |  |  |  |
|  | 17 | 65-70 | 3 | M | 55 | 1.5 | C | 40 | 1.5 | C |
|  | 18 | 90 | 3 | M | 50 | 1 | M |  | Negative |  |
|  |  |  |  |  | 50 | 1 | C |  |  |  |
| ER−/PR− GOOD OUTCOME | 19 | 100 | 2-3 | M | 70 | 1 | M | 20 | 1.5 | M |
|  |  |  |  |  | 70 | 1 | C |  |  |  |
|  | 20 | 90 | 3 | M | 50 | 1-2 | M | 40-50 | 1.5 | M |
|  |  |  |  |  | 70 | 3 | C |  |  |  |
|  | 21 | 80 | 3 | M | 60 | 1-2 | M |  | Negative |  |
|  |  |  |  |  | 70 | 1 | C |  |  |  |
|  | 22 | 40 | 2.5 | M | 95 | 1.5 | C |  | Negative |  |
|  |  |  |  |  | 60 | 1.5 | M |  |  |  |
|  | 23 | 95 | 3 | M | 60 | 2-3 | M | 70 | 2 | M |
|  |  |  |  |  | 90 | 2-3 | C |  |  |  |
|  | 24 | 95 | 3 | M | 50 | 1.5 | C |  | Negative |  |
|  |  |  |  |  | 20 | 1.5 | M |  |  |  |
|  | 25 | 90 | 3 | M |  | Negative |  |  | Negative |  |
|  | 26 | 95 | 3 | M | 10 | 1.5 | M | 25 | 1.5 | M |

TABLE 2-continued

|  | Serial No of Patients | Antibody A CD44 | | | Antibody B CD24 | | | Antibody F ABCC4 | | |
|---|---|---|---|---|---|---|---|---|---|---|
|  |  | % of cells | intensity | location | % of cells | intensity | location | % of cells | intensity | location |
|  | 27 | 80 | 3 | M | 45 | 1.5 | C | 85 | 3 | M |
|  |  |  |  |  | 35 | 1.5 | M |  |  |  |
| ER−/PR− BAD OUTCOME | 28 | <5 | 1 | M | 60-70 | 1-2 | M | 30 | 1.5 | M |
|  |  |  |  |  | 40 | 1-2 | C |  |  |  |
|  | 29 | 75 | 3 | M | 20 | 1-2 | C | 60 | 2 | M |
|  |  | 20 | EACH | C |  |  |  | 20 | 2 | C |
|  | 30 | 5 | 1-2 | M | 50 | 2-3 | M | Negative | | |
|  |  |  |  |  | 90 | 2-3 | C |  |  |  |
|  | 31 | 30 | 2.5 | M | 40 | 2-3 | M | 20 | 1.5 | M |
|  |  | 50 | 2 | C | 60 | 2-3 | C |  |  |  |
|  | 32 | 70 | 1.5 | M | 95 | 2.5 | C | 60 | 1.5 | M |
|  |  | 40 | 1.5 | C | 55 | 1.5 | M |  |  |  |
|  | 33 | 60 | 2.5 | M | 95 | 2 | C | 80 | 2.5 | M |
|  |  | 40 | 1.5 | C | 50 | 2 | M |  |  |  |
|  | 34 | 45 | 2.5 | M | 90 | 1.5 | C | 60 | 1.5 each | C |
|  |  | 30 | 1.5 | C | 45 | 1.5 | M | 35 |  | M |
|  | 35 | 30 | 2.5 | M | Negative | | | 50 | 1.5 | C |
|  | 36 | 35 | 3 | M | 50 | 2 | C | 75 | 1.5 | C |
|  |  | 15 | 1-2 | C | 30 | 1.5 | M | 55 | EACH | M |

TABLE 2A

| ER/PR Status | Outcome | Expression level and location | | | Potential use |
|---|---|---|---|---|---|
|  |  | Marker A | Marker B | Marker F |  |
| P/P | Good | Low expression in M 65 | Moderately high when expression in C alone 91.5 When expressed in MC, C is higher than M M-65 C-108 | Low when expression in M alone 49 When expressed in MC, C is higher than M M-56 C-72 | Less aggressive follow-up |
|  | Bad | High expression in M 213 | Moderate when expression in C alone 142 When expressed in MC, C is higher than M M-57 C-82 | Low when expression in C alone 67.5 Moderate when expression in M alone 135 When expressed in MC, C is much higher than M M-100 C-270 When compared to ER+GOOD | More aggressive treatment |
| N/N | Good | High expression in M 238 | When expressed in MC, C is higher than M M-82 C-119 | Moderate expression in M 98 OR No Expression at all | Less aggressive treatment |
|  | Bad | Low when expression in M alone 20 When expressed in MC, M is much higher than C | When expressed in MC, C is much higher than M M-91 C-148 | Moderate when expression in M alone 86 When expressed in MC, C is higher than M M-85 | Clues for better follow-up |

TABLE 2A-continued

| ER/PR Status | Outcome | Expression level and location | | | Potential use |
|---|---|---|---|---|---|
| | | Marker A | Marker B | Marker F | |
| | | M-131 C-58.5 | | C-88 | |

Expression of A/CD44 should be scored at the invasive edge and not at DCIS edge
M: cell membrane
C: cytoplasm
N: nucleus
NM: Nuclear membrane Table 2 and 2A Interpretation:

Patient sample is segregated based on ER+/PR+ status as one group and ER−/PR− status as another group. On selection and segregation of such expression, the test sample is checked for the presence of either individual markers or a combination of markers (for example as captured here: CD44 and CD24 in combination with ABCC4 is taken into account) mentioned in Table 2.

The result for good and bad prognosis/outcome should ideally show the marker status after taking into account the expression of staining intensity in conjunction with location of the marker and % of staining as disclosed in Table 2.

A pattern of good/bad outcome as depicted in Table 2A can be arrived at, by correlating the 3 entities namely % of staining, staining intensity and location of the marker in the sample after carrying out the process steps disclosed as aforementioned under Example 1. It is to be noted that it is critical to assess the presence or absence of marker A at invasive edge. It is possible that the entire tumor with DCIS focus has HIGH expression of A but the invasive edge has low or no expression and therefore, this aspect is very important for the interpretation of results for Marker A.

If the results obtained after conducting the aforementioned process steps on the test sample coincide with the marker expression results for good outcome (as disclosed in Table 2), the treatment module followed for the patients having good outcome as per Table 10 (patient history) can be referred to and treatment strategy for such patients will therefore require lesser follow up or less aggressive treatment strategy. However, in case of sample results coinciding with marker expression results for bad outcome (as disclosed in Table 2), then such patients will require more aggressive follow ups along with strategic treatment module to be followed OR an alternate treatment approach needs to be employed or conceived which can essentially comprise developing and administering antibodies specific to these combination of markers (here CD44 and CD24 in combination with ABCC4) to curtail its expression.

Increasingly the world over it has been realised that there is a subset of patients in ER+/PR+ group who tend to have bad outcome. Our above mentioned results can segregate ER+/PR+ women with potential good and bad outcome based on expression of CD44 and CD24. However, a person skilled in the art would be able to comprehend that based on the above mentioned results, one way to treat these patients is to prescribe anti-CD44 antibodies since CD44 is highly expressed in the cell-membrane in these patients with a hope of long term disease free survival. On the other hand, in ER−/PR− patients with potential bad outcome, there is low over all expression of CD44, and so antibodies to CD44 will not help much. Nevertheless, it is important to identify them and treat them appropriately with more targeted drugs, frequent and thorough follow-ups etc. to ensure long term disease free survival. Similar strategy can be employed for treating cancer patients with varied marker expressions, some of which are illustrated in the tables below.

It is also to be noted that Good outcome from across ER/PR status cannot be combined. As aforementioned, typically +/+ patients are considered good prognosis cases and hence are need not be treated aggressively. Follow ups for +/+ patients can be carried out every 6-12 months which can be too long for the +/+ bad outcome group. Thus, with the aforementioned interpretation of outcome, it can be inferred that there can be more frequent follow-ups to reduce cancer recurrences between two follow-ups, called interval recurrences, especially for the +/+ bad outcome cases/patients. On the other hand −/− cancers are aggressive cancers and hence patients with good outcome need not be aggressively treated. Whereas, −/− patients with bad outcomes, can have more detailed, effective and innovative Follow-ups to catch the metastasis as early as possible and start the treatment.

ABCC4 is a membrane transporter. Cells use it to get the chemotherapy drugs pumped out, hence when the expression of this marker is high the cells tend to be more resistant to CT (chemotherapy). Also, it is been noted that the cytoplasmic expression of this transporter also helps the cells to pump out the drugs which should be kept in mind while treating the patients. Patients with high M or M+C expression of ABCC4 will be more resistant to drugs and hence perhaps are going to have bad prognosis/outcome and therefore should be treated accordingly.

TABLE 3

| | Serial No of Patients | Antibody I Oct-4 | | | Antibody J Sox-2 | | |
|---|---|---|---|---|---|---|---|
| | | % of cells | Intensity | location | % of cells | intensity | location |
| ER+/PR+ GOOD OUTCOME | 1 | 90 | 3 | N | 20 | 3 | N |
| | 2 | | Negative | | | Negative | |
| | 3 | | Negative | | | Negative | |
| | 4 | | Negative | | 15 | 2.5 | N |
| | 5 | | Negative | | 40 | 3 | N |
| | 6 | | Negative | | 40 | 3 | N |
| | 7 | 60 | 3 | N | | Negative | |

TABLE 3-continued

| | Serial No of Patients | Antibody I Oct-4 | | | Antibody J Sox-2 | | |
|---|---|---|---|---|---|---|---|
| | | % of cells | Intensity | location | % of cells | intensity | location |
| | 8 | | Negative | | | Negative | |
| | 9 | | Negative | | | Negative | |
| ER+/PR+ | 10 | 70 | 2-3 | N | | Negative | |
| BAD | 11 | 90 | 3 | N | | Negative | |
| OUTCOME | 12 | 70 | 2-3 | N | | Negative | |
| | 13 | 65 | 1-2 | C | | Negative | |
| | 14 | 30 | 1-2 | N | | Negative | |
| | 15 | 75 | 1-2 | N | | Negative | |
| | 16 | 30-35 | 3 | N | | Negative | |
| | 17 | 25-30 | 1-2 | N | | Negative | |
| | 18 | 80 | 3 | N | | Negative | |
| ER−/PR− | 19 | 65 | 1-2 | N | 25 | 3 | N |
| GOOD | 20 | | Negative | | | Negative | |
| OUTCOME | 21 | | Negative | | 10 | 3 | N |
| | 22 | | Negative | | 10 | 3 | N |
| | 23 | | Negative | | | Negative | |
| | 24 | | Negative | | | Negative | |
| | 25 | 75 | 1-2 | N | | Negative | |
| | 26 | | Negative | | 80 | 3 | N |
| | 27 | 15 | 1-2 | N | | Negative | |
| ER−/PR− | 28 | 80 | 2.5 | N | 45 | 3 | N |
| BAD | 29 | 40 | 1-2 | N | 25 | 3 | N |
| OUTCOME | 30 | | Negative | | 50 | 3 | N |
| | 31 | | Negative | | | Negative | |
| | 32 | 25 | 1-2 | N | | Negative | |
| | 33 | 20 | 1-2 | N | | Negative | |
| | 34 | 25 | 2 | N | | Negative | |
| | 35 | 20 | 3 | N | 10 | 3 | N |
| | 36 | 55 | 1-2 | N | | Negative | |

TABLE 3A

| ER/PR Status | Outcome | Expression level and location | | Potential use |
|---|---|---|---|---|
| | | Marker I | Marker J | |
| P/P | Good | No expression at all | Moderate expression in N 84 Or NO expression at all | Less aggressive follow-up |
| | Bad | Moderate expression in N 118 | No expression at all treatment | More aggressive |
| N/N | Good | Low expression in N 78 Or NO expression at all | Moderate expression in N 93 Or NO expression at all | Less aggressive treatment |
| | Bad | Low expression in N 76 | Moderate expression in N 98 Or NO expression at all | Clues for better follow-up |

M: cell membrane
C: cytoplasm
N: nucleus
NM: Nuclear membrane

Table 3 and 3A Interpretation:

Patient sample is segregated based on ER+/PR+ status as one group and ER−/PR− status as another group. On selection and segregation of such expression, the test sample is checked for the presence of either individual markers or a combination of markers (for example as captured here: Oct-4 in combination with Sox-2 is taken into account) mentioned in Table 3.

The result for good and bad prognosis/outcome should ideally show the marker status after taking into account the expression of staining intensity in conjunction with location of the marker and % of staining as disclosed in Table 3.

A pattern of good/bad outcome as depicted in Table 3A can be arrived at, by correlating the 3 entities namely % of staining, staining intensity and location of the marker in the sample after carrying out the process steps disclosed as aforementioned under Example 1.

If the results obtained after conducting the aforementioned process steps on the test sample coincide with the marker expression results for good outcome (as disclosed in Table 3), the treatment module followed for the patients having good outcome as per Table 10 (patient history) can be referred to and treatment strategy for such patients will therefore require lesser follow up or less aggressive treatment strategy. However, in case of sample results coinciding with marker expression results for bad outcome (as disclosed in Table 3), then such patients will require more aggressive follow ups along with strategic treatment module to be followed OR an alternate treatment approach needs to be employed or conceived which can essentially comprise developing and administering antibodies specific to these combination of markers (here Oct-4 and Sox-2) to curtail its expression.

It is also to be noted that Good outcome from across ER/PR status cannot be combined. As aforementioned, typically +/+ patients are considered good prognosis cases and hence are need not be treated aggressively. Follow ups for +/+ patients can be carried out every 6-12 months which can be too long for the +/+ bad outcome group. Thus, with the aforementioned interpretation of outcome, it can be inferred that there can be more frequent follow-ups to reduce cancer recurrences between two follow-ups, called interval recurrences, especially for the +/+ bad outcome cases/patients. On the other hand −/− cancers are aggressive cancers and hence patients with good outcome need not be aggressively treated. Whereas, −/− patients with bad outcomes, can have more detailed, effective and innovative Follow-ups to catch the metastasis as early as possible and start the treatment.

TABLE 4

| | Serial No of Patients | Antibody K APC | | | Antibody 0 B-Catenin | | |
|---|---|---|---|---|---|---|---|
| | | % of cells | Intensity | Location | % of cells | Intensity | Location |
| ER+/PR+ GOOD OUTCOME | 1 | 60 | 2 | M | 35-40 | 1-2 EACH | N |
| | | 80 | 3 | C | 45 | | M |
| | | 30 | 3 | N | | | |
| | 2 | 70 | 2 | C | 15 | 1-2 | M |
| | | | | | 10 | 2 | N |
| | 3 | 85 | 3 | C | | Negative | |
| | | 50 | 2 | M | | | |
| | 4 | 85 | 2 | C | 20 | 1.5 | M |
| | | 70 | 2-3 | NM | | | |
| | 5 | 60 | 2 | M | — | | |
| | | 90 | 2.5 | C | | | |
| | 6 | 10 | 1-2 | M | | Negative | |
| | | 90 | 3 | C | | | |
| | 7 | 80 | 3 | C | 10 | 2 | N |
| | | 30 | 2-3 | M | | | |
| | 8 | 90 | 3 | C | | Negative | |
| | | 50 | 3 | N | | | |
| | 9 | 75 | 2 | M | 35 | 1.5 | M |
| | | 30 | 1-2 | C | | | |
| ER+/PR+ BAD OUTCOME | 10 | 80 | 3 | C | 50 | 1.5 | C |
| | | 50 | 2-3 | NM | | | |
| | 11 | 65 | 2 | M | 80 | 2 | M |
| | | 85 | 2.5 | C | | | |
| | | 65 | 2.5 | NM | | | |
| | 12 | 60 | 2 | M | 50 | 2 | C |
| | | 80 | 2 | C | 25-30 | 1-2 | M |
| | 13 | 90 | 3 | C | | — | |
| | 14 | 70 | 3 | C | 20 | 1.5 | M |
| | | 60 | 2-3 | M | | | |
| | 15 | 90 | 2-3 | C | | — | |
| | | 50 | 2 | M | | | |
| | 16 | 70 | 1-2 | C | | — | |
| | | 60 | 2 | N | | | |
| | 17 | 50 | 1-2 | C | 40 | 2 | M |
| | 18 | 80 | 2.5 | C | 65 | 3 | M |
| | | 50 | 2.5 | NM | | | |
| ER−/PR− GOOD OUTCOME | 19 | 30 | 2 | M | 75 | 1-2 | M |
| | | 60 | 1-2 | C | | | |
| | 20 | 70 | 2-3 | M | 60 | 1-2 | M |
| | | 90 | 2-3 | C | | | |
| | 21 | 50 | 2 | M | 20 | 1-2 | M |
| | | 70 | 1.5 | C | | | |
| | 22 | 60 | 3 | C | 50 | 1.5 | C |
| | | 60 | 2 | M | | | |
| | 23 | 90 | 3 | C | 75 | 1-2 | M |
| | | 80 | 2.5 | M | | | |
| | 24 | 85 | 3 | C | | — | |
| | | 75 | 2-3 | M | | | |
| | 25 | 85 | 3 | C | | — | |
| | | 30 | 2 | M | | | |
| | 26 | 80 | 1-2 | C | | Negative | |
| | 27 | 70 | 2 | C | 60 | 3 | M |
| | | 70 | 2 | M | | | |
| ER−/PR− BAD OUTCOME | 28 | 80 | 2-3 | M | 50 | 1-2 | M |
| | | 55 | 1.5 | C | | | |
| | 29 | 40 | 1.5 | C | 60 | 2 | M |
| | | 40 | 2 | M | | | |
| | 30 | 90 | 2-3 | C | 60 | 1-2 | M |
| | | 40 | 2 | M | | | |
| | | 65 | 2.5 | NM | | | |
| | 31 | 95 | 3 | C | 60 | 1-2 | M |
| | | 60 | 2-3 | M | | | |
| | 32 | 80 | 3 | C | 75 | 2 | M |
| | | 70 | 2-3 | M | | | |
| | | 50 | 2-3 | NM | | | |
| | 33 | 90 | 3 | C | 80 | 1.5 EACH | C |
| | | 85 | 2 | M | 40 | | M |
| | 34 | 95 | 3 | C | | — | |
| | | 60 | 2 | M | | | |
| | 35 | 30 | 1-2 | C | | — | |
| | 36 | 90 | 2 | C | | Negative | |

TABLE 4A

| ER/PR Status | Outcome | Expression level and location | | Potential use |
|---|---|---|---|---|
| | | Marker K | Marker O | |
| P/P | Good | When expressed in MC, C is much higher than M<br>M-86<br>C-225<br>Expression also seen in N in various levels | Low when expression in M alone<br>41<br>When expressed in N and M, M and N are almost equally expressed<br>M-45<br>N-43 | Less aggressive follow-up |
| | Bad | Moderate when expression in C alone<br>140<br>When expressed in MC, C is higher than M<br>M-114<br>C-200<br>When expressed in C-NM, C is higher than NM<br>NM-138<br>C-246 | Moderate expression in M<br>102<br>Expression in C is also seen | More aggressive treatment |
| N/N | Good | When expressed in MC, C is higher than M<br>M-116<br>C-152 | Moderate expression in M alone<br>104 | Less aggressive treatment |
| | Bad | When expressed in MC, C is higher than M<br>M-130<br>C-150<br>Moderate when expression in C alone<br>108<br>When expressed in C, M and NM, C is highest, followed by NM and M<br>M-110<br>NM-145<br>C-238 | Moderate expression in M alone<br>104 | Clues for better follow-up |

M: cell membrane
C: cytoplasm
N: nucleus
NM: Nuclear membrane

Table 4 and 4A Interpretation:

Patient sample is segregated based on ER+/PR+ status as one group and ER−/PR− status as another group. On selection and segregation of such expression, the test sample is checked for the presence of either individual markers or a combination of markers (for example as captured here: APC in combination with B-Catenin is taken into account) mentioned in Table 4.

The result for good and bad prognosis/outcome should ideally show the marker status after taking into account the expression of staining intensity in conjunction with location of the marker and % of staining as disclosed in Table 4.

A pattern of good/bad outcome as depicted in Table 4A can be arrived at, by correlating the 3 entities namely % of staining, staining intensity and location of the marker in the sample after carrying out the process steps disclosed as aforementioned under Example 1.

If the results obtained after conducting the aforementioned process steps on the test sample coincide with the marker expression results for good outcome (as disclosed in Table 4), the treatment module followed for the patients having good outcome as per Table 10 (patient history) can be referred to and treatment strategy for such patients will therefore require lesser follow up or less aggressive treatment strategy. However, in case of sample results coinciding with marker expression results for bad outcome (as disclosed in Table 4), then such patients will require more aggressive follow ups along with strategic treatment module to be followed OR an alternate treatment approach needs to be employed or conceived which can essentially comprise developing and administering antibodies specific to these combination of markers (here APC and B-Catenin) to curtail its expression.

It is also to be noted that Good outcome from across ER/PR status cannot be combined. As aforementioned, typically +/+ patients are considered good prognosis cases and hence are need not be treated aggressively. Follow ups for +/+ patients can be carried out every 6-12 months which can be too long for the +/+ bad outcome group. Thus, with the aforementioned interpretation of outcome, it can be inferred that there can be more frequent follow-ups to reduce cancer recurrences between two follow-ups, called interval recurrences, especially for the +/+ bad outcome cases/patients. On the other hand −/− cancers are aggressive cancers and hence patients with good outcome need not be aggressively treated. Whereas, −/− patients with bad outcomes, can have more detailed, effective and innovative Follow-ups to catch the metastasis as early as possible and start the treatment.

TABLE 5

|  | Serial No of Patients | Antibody G CD133 | | |
|---|---|---|---|---|
|  |  | % of cells | Intensity | Location |
| ER+/PR+ GOOD OUTCOME | 1 | 60 | 2.5 | N |
|  |  | 30 | 1.5 | M |
|  | 2 | 50 | 1.5 | C |
|  | 3 | 90 | 1.5 EACH | C |
|  |  | 20 |  | M |
|  | 4 | 30-35 | 2 | M |
|  |  | 50 | 1.5 | C |
|  | 5 | 70 | 2 | M |
|  |  | 50 | 2 | C |
|  | 6 | 50 | 2 | M |
|  |  | 60 | 2 | C |
|  | 7 | 40 | 2 | M |
|  |  | 70 | 2-3 | C |
|  | 8 | 45 | 1-2 | C |
|  | 9 | 65 | 2 | M |
| ER+/PR+ BAD OUTCOME | 10 | 80 | 1.5 | C |
|  | 11 | 60 | 1-2 | C |
|  | 12 | 25 | 2 | M |
|  |  | 80 | 2 | C |
|  | 13 | 80 | 2 | C |
|  | 14 | 90 | 2 | M |
|  |  | 30 | 1.5 | C |
|  | 15 | 70 | 1.5 EACH | M |
|  |  | 30 |  | C |
|  | 16 | 15 | 1.5 EACH | M |
|  |  | 35 |  | C |
|  | 17 | 30 | 1.5 | M |
|  | 18 |  | Negative |  |
| ER−/PR− GOOD OUTCOME | 19 |  | NEGATIVE |  |
|  | 20 | 70 | 2 | M |
|  |  | 60 | 2 | C |
| ER−/PR− | 21 | 25 | 1-2 | M |
|  | 22 | 65 | 1.5 each | C |
|  |  | 65 |  | M |
|  | 23 | 55 | 2 | M |
|  |  | 75 | 2 | C |
|  | 24 | 60 | 2 | M |
|  |  | 25 | 1-2 | C |
|  | 25 | 60 | 1.5 | C |
|  |  | 40 | 1.5 | M |
|  | 26 | 20 | 1.5 | M |
|  | 27 | 55 | 1.5 EACH | C |
|  |  | 45 |  | M |
| ER−/PR− BAD OUTCOME | 28 | 60 | 1-2 | M |
|  |  | 30 | 1-2 | C |
| ER−/PR− | 29 | 20 | 2 | M |
|  |  | 20 | 2 | C |
|  | 30 | 50 | 1.5 Each | M |
|  |  | 50 |  | C |
|  | 31 | 55 | 1.5 Each | C |
|  |  | 10 |  | M |
|  | 32 | 70 | 2 | M |
|  |  | 45 | 1.5 | C |
|  | 33 | 80 | 2 each | C |
|  |  | 75 |  | M |
|  | 34 | 65 | 2 | C |
|  | 35 | 40 | 2 | C |
|  |  | 20 | 3 | N |
|  | 36 | 50 | 2 | C |

TABLE 6

|  | Serial No of Patients | Antibody L P-Cadherin | | |
|---|---|---|---|---|
|  |  | % of cells | Intensity | Location |
| ER+/PR+ GOOD OUTCOME | 1 | 20 | 2-3 | M |
|  | 2 |  | Negative |  |
|  | 3 |  | Negative |  |
|  | 4 | 20 | 2 | M |
|  | 5 |  | Negative |  |
|  | 6 |  | Negative |  |
|  | 7 | 50 | 3 | M |
|  | 8 | 10 | 3 | M |
|  | 9 | 40 | 3 | M |
| ER+/PR+ BAD OUTCOME | 10 | 20 | 3 | M |
|  | 11 | 80 | 3 | M |
|  | 12 | 20 | 3 | M |
|  | 13 |  | Negative |  |
|  | 14 |  | Negative |  |
|  | 15 | 90 | 3 | M |
|  | 16 | 30 | 2.5 | M |
|  | 17 | 45 | 2.5 | M |
|  | 18 | 90-100 | 3 | M |
| ER−/PR− GOOD OUTCOME | 19 | 50 | 3 | M |
|  | 20 | 55 | 3 | M |
|  | 21 | 50 | 3 | M |
| ER−/PR− | 22 | 80 | 3 | M |
|  | 23 | 70 | 2 | M |
|  | 24 | 70 | 3 | M |
|  | 25 | 65-70 | 3 | M |
|  | 26 |  | Negative |  |
|  | 27 | 80 | 3 | M |
| ER−/PR− BAD OUTCOME | 28 | 80 | 3 | M |
|  | 29 | 15-20 | 3 | M |
|  | 30 | 15 | 3 | M |
| ER−/PR− | 31 |  | Negative |  |
|  | 32 | 20 | 3 | M |
|  | 33 | 75 | 3 | M |
|  | 34 | <5 | 3 | M |
|  | 35 | 45 | 2.5 | M |
|  | 36 |  | Negative |  |

TABLE 6A

| ER/PR Status | Outcome | Expression level and location Marker L | Potential use |
|---|---|---|---|
| P/P | Good | Moderate expression in M 84 | Less aggressive follow-up |
|  | Bad | High expression in M 162 | More aggressive treatment |
| N/N | Good | High expression in M 195 | Less aggressive treatment |
|  | Bad | Moderate expression in M 111 | Clues for better follow-up |

M: cell membrane
C: cytoplasm
N: nucleus
NM: Nuclear membrane

Table 6 and 6A Interpretation:

Patient sample is segregated based on ER+/PR+ status as one group and ER−/PR− status as another group. On selection and segregation of such expression, the test sample is checked for the presence of either individual markers or a combination of markers (for example as captured here: P-cadherin alone is taken into account) mentioned in Table 6.

The result for good and bad prognosis/outcome should ideally show the marker status after taking into account the expression of staining intensity in conjunction with location of the marker and % of staining as disclosed in Table 6.

A pattern of good/bad outcome as depicted in Table 6A can be arrived at, by correlating the 3 entities namely % of staining, staining intensity and location of the marker in the sample after carrying out the process steps disclosed as aforementioned under Example 1.

If the results obtained after conducting the aforementioned process steps on the test sample coincide with the marker expression results for good outcome (as disclosed in Table 6), the treatment module followed for the patients having good outcome as per Table 10 (patient history) can be referred to and treatment strategy for such patients will therefore require lesser follow up or less aggressive treatment strategy. However, in case of sample results coinciding with marker expression results for bad outcome (as disclosed in Table 6), then such patients will require more aggressive follow ups along with strategic treatment module to be followed OR an alternate treatment approach needs to be employed or conceived which can essentially comprise developing and administering antibodies specific to these combination of markers (here P-cadherin alone) to curtail its expression.

Increasingly the world over it has been realised that there is a subset of patients in ER+/PR+ group who tend to have bad outcome. Our above mentioned results can segregate ER+/PR+ women with potential good and bad outcome based on expression of P-cadherin. However, a person skilled in the art would be able to comprehend that based on the above mentioned results, one way to treat these patients is to prescribe anti-P-cadherin antibodies since P-cadherin is highly expressed in the cell-membrane in these patients with a hope of long term disease free survival. On the other hand, in ER−/PR− patients with potential bad outcome, there is lower over all expression of P-cadherin, and so antibodies to P-cadherin will not help much. Nevertheless, it is important to identify them and treat them appropriately with more targeted drugs, frequent and thorough follow-ups etc. to ensure long term disease free survival. Similar strategy can be employed for treating cancer patients with varied marker expressions, some of which are illustrated in the tables below.

It is also to be noted that Good outcome from across ER/PR status cannot be combined. As aforementioned, typically +/+ patients are considered good prognosis cases and hence are need not be treated aggressively. Follow ups for +/+ patients can be carried out every 6-12 months which can be too long for the +/+ bad outcome group. Thus, with the aforementioned interpretation of outcome, it can be inferred that there can be more frequent follow-ups to reduce cancer recurrences between two follow-ups, called interval recurrences, especially for the +/+ bad outcome cases/patients. On the other hand −/− cancers are aggressive cancers and hence patients with good outcome need not be aggressively treated. Whereas, −/− patients with bad outcomes, can have more detailed, effective and innovative Follow-ups to catch the metastasis as early as possible and start the treatment.

TABLE 7

| | Serial No of Patients | Antibody A CD44 | | | Antibody B CD24 | | | Antibody I Oct-4 | | | Antibody J Sox-2 | | |
|---|---|---|---|---|---|---|---|---|---|---|---|---|---|
| | | % of cells | intensity | location | % of cells | intensity | location | % of cells | intensity | location | % of cells | intensity | location |
| ER+/PR+ GOOD OUTCOME | 1 | 20 | 1-2 | M | 60 | 1.5 | M | 90 | 3 | N | 20 | 3 | N |
| | | | | | 80 | 1.5 | C | | | | | | |
| | 2 | 20 | 2-3 | M | 10 | 1.5 | M | Negative | | | Negative | | |
| | | | | | 40 | 1.5 | C | | | | | | |
| | 3 | | Negative | | 55 | 1.5 | C | Negative | | | <5% | 2-3 | N |
| | 4 | 35 | 2 | M | 65-70 | 1.5 | C | Negative | | | 15 | 2.5 | N |
| | 5 | 5 | 3 | M | 85 | 3 | M | Negative | | | 40 | 3 | N |
| | | | | | 50 | 2 | C | | | | | | |
| | 6 | 40 | 2-3 | M | 80 | 2-3 | C | Negative | | | 40 | 3 | N |
| | | | | | 20 | 1-2 | M | | | | | | |
| | 7 | 40 | 3 | M | 35-40 | 3 | C | 60 | 3 | N | Negative | | |
| | | | | | 25-30 | 2 | M | | | | | | |
| | 8 | 10 | 1.5 | C | 75 | 2 | C | Negative | | | Negative | | |
| | | | | | 35-40 | 1.5 | M | | | | | | |
| | 9 | 20 | 3 | M | 25 | 1.5 | M | Negative | | | Negative | | |
| | | | | | 15 | EACH | C | | | | | | |
| ER+/PR+ BAD OUTCOME | 10 | 20 | 1.5 | M | 95 | 1.5 | C | 70 | 2-3 | N | Negative | | |
| | | 60 | 2 | C | | | | | | | | | |
| | 11 | 95 | 3 | M | <10 | 1 | M | 90 | 3 | N | Negative | | |
| | | | | | 90 | 1 | C | | | | | | |
| | 12 | 70 | 3 | M | 50 | 2-3 | M | 70 | 2-3 | N | 5 | 3 | N |
| | | | | | 70 | 1-2 | C | | | | | | |
| | 13 | 90 | 2.5 | M | 95 | 2.5 | C | 65 | 1-2 | C | Negative | | |
| | 14 | 75 | 1.5 | M | 95 | 1.5 | C | 30 | 1-2 | N | Negative | | |
| | | | | | 80 | 1.5 | M | | | | | | |
| | 15 | 60 | 2.5 | M | 70 | 1.5 | C | 75 | 1-2 | N | Negative | | |
| | 16 | 80-85 | 3 | M | 10 | 1.5 | C | 30-35 | 3 | N | Negative | | |
| | | | | | 20 | 2 | M | | | | | | |
| | 17 | 65-70 | 3 | M | 55 | 1.5 | C | 25-30 | 1-2 | N | Negative | | |
| | 18 | 90 | 3 | M | 50 | 1 | M | 80 | 3 | N | Negative | | |
| | | | | | 50 | 1 | C | | | | | | |
| ER−/PR− GOOD OUTCOME | 19 | 100 | 2-3 | M | 70 | 1 | M | 65 | 1-2 | N | 25 | 3 | N |
| | | | | | 70 | 1 | C | | | | | | |
| | 20 | 90 | 3 | M | 50 | 1-2 | M | Negative | | | Negative | | |
| | | | | | 70 | 3 | C | | | | | | |
| | 21 | 80 | 3 | M | 60 | 1-2 | M | Negative | | | 10 | 3 | N |
| | | | | | 70 | 1 | C | | | | | | |
| | 22 | 40 | 2.5 | M | 95 | 1.5 | C | Negative | | | 10 | 3 | N |
| | | | | | 60 | 1.5 | M | | | | | | |

TABLE 7-continued

| | Serial No of Patients | Antibody A CD44 | | | Antibody B CD24 | | | Antibody I Oct-4 | | | Antibody J Sox-2 | | |
|---|---|---|---|---|---|---|---|---|---|---|---|---|---|
| | | % of cells | intensity | location | % of cells | intensity | location | % of cells | intensity | location | % of cells | intensity | location |
| | 23 | 95 | 3 | M | 60 | 2-3 | M | | Negative | | | Negative | |
| | | | | | 90 | 2-3 | C | | | | | | |
| ER−/PR− GOOD OUTCOME | 24 | 95 | 3 | M | 50 | 1.5 | C | | Negative | | <5 | 2-3 | N |
| | | | | | 20 | 1.5 | M | | | | | | |
| | 25 | 90 | 3 | M | | Negative | | 75 | 1-2 | N | | Negative | |
| | 26 | 95 | 3 | M | 10 | 1.5 | M | | Negative | | 80 | 3 | N |
| | 27 | 80 | 3 | M | 45 | 1.5 | C | 15 | 1-2 | N | | Negative | |
| | | | | | 35 | 1.5 | M | | | | | | |
| ER−/PR− BAD OUTCOME | 28 | <5 | 1 | M | 60-70 | 1-2 | M | 80 | 2.5 | N | 45 | 3 | N |
| | | | | | 40 | 1-2 | C | | | | | | |
| | 29 | 75 | 3 | M | 20 | 1-2 | C | 40 | 1-2 | N | 25 | 3 | N |
| | | 20 | EACH | C | | | | | | | | | |
| | 30 | 5 | 1-2 | M | 50 | 2-3 | M | | Negative | | 50 | 3 | N |
| | | | | | 90 | 2-3 | C | | | | | | |
| | 31 | 30 | 2.5 | M | 40 | 2-3 | M | | Negative | | | | |
| | | 50 | 2 | C | 60 | 2-3 | C | | | | | | |
| | 32 | 70 | 1.5 | M | 95 | 2.5 | C | 25 | 1-2 | N | Negative | <5% | — |
| | | 40 | 1.5 | C | 55 | 1.5 | M | | | | | | |
| | 33 | 60 | 2.5 | M | 95 | 2 | C | 20 | 1-2 | N | | Negative | |
| | | 40 | 1.5 | C | 50 | 2 | M | | | | | | |
| | 34 | 45 | 2.5 | M | 90 | 1.5 | C | 25 | 2 | N | | Negative | |
| | | 30 | 1.5 | C | 45 | 1.5 | M | | | | | | |
| | 35 | 30 | 2.5 | M | | Negative | | 20 | 3 | N | 10 | 3 | N |
| | 36 | 35 | 3 | M | 50 | 2 | C | 55 | 1-2 | N | | Negative | |
| | | 15 | 1-2 | C | 30 | 1.5 | M | | | | | | |

TABLE 7A

| ER/PR Status | Outcome | Expression level and location | | | | Potential use |
|---|---|---|---|---|---|---|
| | | Marker A | Marker B | Marker I | Marker J | |
| P/P | Good | Low expression in M 65 | Moderately high when expression in C alone 91.5 When expressed in MC, C is higher than M M-65 C-108 | No expression at all | Moderate expression in N 84 Or NO expression at all | Less aggressive follow-up |
| | Bad | High expression in M 213 | Moderate when expression in C alone 142 When expressed in MC, C is higher than M M-57 C-82 | Moderate expression in N 118 | No expression at all | More aggressive treatment |
| N/N | Good | High expression in M 238 | When expressed in MC, C is higher than M M-82 C-119 | Low expression in N 78 Or NO expression at all | Moderate expression in N 93 Or NO expression at all | Less aggressive treatment |
| | Bad | Low when expression in M alone 20 When expressed in MC, M is much higher than C | When expressed in MC, C is much higher than M M-91 C-148 | Low expression in N 76 | Moderate expression in N 98 Or NO expression at all | Clues for better follow-up |

TABLE 7A-continued

| ER/PR Status | Outcome | Expression level and location | | | | Potential use |
|---|---|---|---|---|---|---|
| | | Marker A | Marker B | Marker I | Marker J | |
| | | M-131 C-58.5 | | | | |

Expression of A/CD44 should be scored at the invasive edge and not at DCIS edge
M: cell membrane
C: cytoplasm
N: nucleus
NM: Nuclear membrane Table 7 and 7A Interpretation:

Patient sample is segregated based on ER+/PR+ status as one group and ER−/PR− status as another group. On selection and segregation of such expression, the test sample is checked for the presence of either individual markers or a combination of markers (for example as captured here: CD44 in combination with CD24, Oct-4 and Sox-2 is taken into account) mentioned in Table 7.

The result for good and bad prognosis/outcome should ideally show the marker status after taking into account the expression of staining intensity in conjunction with location of the marker and % of staining as disclosed in Table 7.

A pattern of good/bad outcome as depicted in Table 7A can be arrived at, by correlating the 3 entities namely % of staining, staining intensity and location of the marker in the sample after carrying out the process steps disclosed as aforementioned under Example 1. It is to be noted that it is critical to assess the presence or absence of marker A at invasive edge. It is possible that the entire tumor with DCIS focus has HIGH expression of A but the invasive edge has low or no expression and therefore, this aspect is very important for the interpretation of results for Marker A.

If the results obtained after conducting the aforementioned process steps on the test sample coincide with the marker expression results for good outcome (as disclosed in Table 7), the treatment module followed for the patients having good outcome as per Table 10 (patient history) can be referred to and treatment strategy for such patients will therefore require lesser follow up or less aggressive treatment strategy. However, in case of sample results coinciding with marker expression results for bad outcome (as disclosed in Table 7), then such patients will require more aggressive follow ups along with strategic treatment module to be followed OR an alternate treatment approach needs to be employed or conceived which can essentially comprise developing and administering antibodies specific to these combination of markers (here CD44 in combination with CD24, Oct-4 and Sox-2) to curtail its expression Increasingly the world over it has been realised that there is a subset of patients in ER+/PR+ group who tend to have bad outcome. Our above mentioned results can segregate ER+/PR+ women with potential good and bad outcome based on expression of CD44 and CD24. However, a person skilled in the art would be able to comprehend that based on the above mentioned results, one way to treat these patients is to prescribe anti-CD44 antibodies since CD44 is highly expressed in the cell-membrane in these patients with a hope of long term disease free survival. On the other hand, in ER−/PR− patients with potential bad outcome, there is low over all expression of CD44, and so antibodies to CD44 will not help much. Nevertheless, it is important to identify them and treat them appropriately with more targeted drugs, frequent and thorough follow-ups etc. to ensure long term disease free survival. Similar strategy can be employed for treating cancer patients with varied marker expressions, some of which are illustrated in the tables below.

It is also to be noted that Good outcome from across ER/PR status cannot be combined. As aforementioned, typically +/+ patients are considered good prognosis cases and hence are need not be treated aggressively. Follow ups for +/+ patients can be carried out every 6-12 months which can be too long for the +/+ bad outcome group. Thus, with the aforementioned interpretation of outcome, it can be inferred that there can be more frequent follow-ups to reduce cancer recurrences between two follow-ups, called interval recurrences, especially for the +/+ bad outcome cases/patients. On the other hand −/− cancers are aggressive cancers and hence patients with good outcome need not be aggressively treated. Whereas, −/− patients with bad outcomes, can have more detailed, effective and innovative Follow-ups to catch the metastasis as early as possible and start the treatment.

TABLE 8

| | Serial No of Patients | Antibody C ABCG2 | | |
|---|---|---|---|---|
| | | % of cells | Intensity | Location |
| ER+/PR+ GOOD OUTCOME | 1 | 95 | 3 | N |
| | | 30 | 1.5 | M |
| | 2 | 75 | 3 | N |
| | 3 | 95 | 1.5 | C |
| | | 35 | 1.5 | M |
| | 4 | 90 | 2.5 | C |
| | | 35 | 1.5 | M |
| | 5 | 50 | 2 | M |
| | | 80 | 2 | C |
| | 6 | <5 | 2 | M |
| | | 80 | 2-3 | C |
| | 7 | 80 | 3 | N |
| | | 60 | 3 | C |
| | 8 | 90 | 3 | N |
| | | 70 | 2 | C |
| | | 10 | 1-2 | M |
| | 9 | 45 | 3 | N |
| | | 35 | 2 | M |
| ER+/PR+ BAD OUTCOME | 10 | 95 | 1.5 EACH | C |
| | | 45 | | N |
| | 11 | 80 | 2 | C |
| | | 90 | 3 | N |
| | 12 | 20 | 1.5 | M |
| | | 50 | 1.5 | C |
| | | 40 | 2.5 | N |
| | 13 | 90 | 2.5 | C |
| | 14 | 90 | 1.5 | C |
| | | 70 | 1.5 | M |
| | 15 | 95 | 1.5 EACH | N |
| | | 95 | | C |
| | | 20 | | M |
| | 16 | 30 | 3 | N |
| | 17 | 60 | 2 | C |
| | | 80 | 3 | N |

TABLE 8-continued

| | Serial No of Patients | Antibody C ABCG2 | | |
|---|---|---|---|---|
| | | % of cells | Intensity | Location |
| | 18 | 50 | 1.2 | C |
| | | 80 | 3 | N |
| ER−/PR− GOOD OUTCOME ER−/PR− | 19 | 80 | 3 | Nu |
| | 20 | 40 | 2 | M |
| | | 80 | 2-3 | C |
| | | 75 | 3 | Nu |
| | 21 | 65 | 2.5 | N |
| | | 40 | 1.5 | C |
| | | 30 | 2 | M |
| | 22 | 75 | 1.5 | N |
| | | 90 | 1.5 | C |
| | | 65 | 1.5 | M |
| | 23 | 30 | 2 | M |
| | | 65 | 3 | C |
| | 24 | 85 | 1.5 | C |
| | | 50 | 1.5 | M |
| | 25 | 75 | 2.5 | N |
| | | 80 | 1.5 | C |
| | | 20 | 1.5 | M |
| | 26 | 45 | 2 | N |
| | 27 | 95 | 2 | C |
| | | 20 | 2 | N |
| | | 20 | 2 | M |
| ER−/PR− BAD OUTCOME ER−/PR− | 28 | 50 | 1.5 each | N |
| | | 65 | | C |
| | | 20 | | M |
| | 29 | 40 | 2-3 | C |
| | | 20 | 3 | Nu |
| | 30 | 70 | 2 | C |
| | 31 | 70 | 2.5 | C |
| | | 10 | 2 | M |
| | 32 | 30 | 2 EACH | N |
| | | 60 | | M |
| | | 40 | | C |
| | 33 | 95 | 1.5 | C |
| | | 10 | 1 | M |
| | 34 | 75 | 1.5 | C |
| | 35 | 80 | 2 | C |
| | | 30 | 3 | N |
| | 36 | 85 | 2 | C |
| | | 40 | 2 | N |

TABLE 9

| | Serial No of Patients | Antibody E ESA | | |
|---|---|---|---|---|
| | | % of cells | Intensity | Location |
| ER+/PR+ GOOD OUTCOME | 1 | 90 | 3 | M |
| | 2 | 90 | 3 | M |
| | 3 | 95 | 3 | M |
| | 4 | 95 | 3 | M |
| | 5 | 90 | 3 | M |
| | 6 | 95 | 3 | M |
| | 7 | 95 | 3 | M |
| | 8 | — | | |
| | 9 | 45 | 3 | M |
| ER+/PR+ BAD OUTCOME | 10 | 95 | 3 | M |
| | 11 | 95 | 3 | M |
| | 12 | 75 | 3 | M |
| | 13 | 95 | 3 | M |
| | 14 | 95 | 3 | M |
| | 15 | 95 | 3 | M |
| | 16 | 90 | 3 | M |
| | 17 | 55 | 3 | M |
| | 18 | 100 | 3 | M |
| ER−/PR− GOOD OUTCOME ER−/PR− | 19 | 85-90 | 3 | M |
| | 20 | 95 | 3 | M |
| | 21 | 90 | 3 | M |
| | 22 | 95 | 3 | M |
| | 23 | 90 | 3 | M |
| | 24 | 95 | 3 | M |
| | 25 | 95 | 3 | M |
| | 26 | 85 | 3 | M |
| | 27 | 35 | 3 | M |
| ER−/PR− BAD OUTCOME ER−/PR− | 28 | 100 | 3 | M |
| | 29 | 50 | 3 | M |
| | 30 | 85 | 3 | M |
| | 31 | 90 | 3 | M |
| | 32 | 95 | 3 | M |
| | 33 | 95 | 3 | M |
| | 34 | 95 | 3 | M |
| | | 70 | 1.5 | C |
| | 35 | 75 | 3 | M |
| | 36 | 90 | 3 | M |

TABLE 10

| Patient history | Serial No of Patients | Age | Stage | Grade | ER/PR/Her2 | MRM/CT/RT | Patient status |
|---|---|---|---|---|---|---|---|
| ER+/PR+ Good Outcome | 1 | 54, Post | IDC-2, small foci DCIS, L Br | T2N2M0, pT2NaM2 | P/P/P | November 2003: MRM; December 2003-April 2004: CT-FAC x6; April 2004: RT; October 2004 on Tamx, c/o lower back ache | No mets and Alive; |
| | 2 | 26 | IDC-2, L Br | T2N0M0 (Stage-2a) | P/P/N | Quadrectomy in November 2004, BCT/RT/CT-FAC, on TAM 20y HS; 2007-Normal, 3 yrs of TAM; December 2009-Normal, TAM to stop after 5 yrs of usage; 2011-All normal | Alive, most likely Ca free |
| | 3 | 44, Premeno. | IDC-3 lymphatic emboli & perineural invasion; R Br | T2N1M0, pT2N3M0 (Stage-3a) | 20% P/20% P | H/o DM, Hypothyroid, HT, Lap. Cholecystectomy; January 2004 Trucut Biopsy; Bone scan-N, MRM; February-June 2004 CT-FEC x6; April 2004 RT; July 2009 on extended Adj Hormonal therapy; June 2010 Anastrozole for 6 yrs L-Mammo: some mass present, no intervention adv.; August 2011: R-Mammo-N, Inj Zolodronic acid. | No mets and alive; |
| | 4 | 48 | IDC-2; L Br | pT2N0M0 | P/P/P | MRM in August 2005; Adj CT-FEC x6 in August-December 2005; December 2005 Start Tamx 20 mg/d x5 yrs; December 2005-January 2006 RT 45 Gy/25# | Alive |
| | 5 | 55, Post | IDC, L Br | T2N2M0 | P/P | December 2002: Exi. Biopsy L Br, MRM, Bone scan-Normal; January-June 2003: High risk CT-AC x6; March-May 2003: RT; June 2003 Started Tamx; March 2009: Breathless, no wt gain, R Br, L MRM - Normal, adv. PET-CT scan | No mets for 6 yrs and alive |
| | 6 | 54, Post | IDC-3, R Br | T2N0M0, pT2N0 | P/P | lump in R br for 2 weeks, MRM May 2003; CT-AC x4 June-August 2003; on Tamoxifen for 7 yrs total & anastrazole for 5 yrs; October 2006 all Normal; September 2008 all normal; July 2009 Fatty changes in liver, February 2011 L br Normal; December 2011 BMD-osteoporosis L & R br Normal, on Zoledromide fro January 2010 till December 2011 | no mets and alive |
| | 7 | 52/54, Post | IDC, L Br | multifocal T1N1M0 | P/P | R Br Lumpectomy in '99, again in 2001 which was found Normal, Post surgery CT/RT; Was put on TAM but stopped and started Tab Anastrazole; Mother had Cancer; Cholecystectomy on 05/04/08 | No mets and alive, R Br in '91, '00(found to be Normal), Mother had cancer |
| | 8 | 62 | IDC-3 | T2N0 | P/P | K/c/o Ca Br; L-MRM March 2005; Adj CT-Taxol x4; Pt on Shelcal; Stazonex, inj Zolastra; anastrazole ect tablets and regular F/up since 2005; Last F/up in July 2011 and next due in July 2012. | Alive and doing well and no mets |
| | 9 | 40 | IDC-III; R Br | T2N1MX | N/P30%/P | Lump in R breast for 6 months; R-MRM on August 2005; Adj CT-TACx6 September-December 2005. Adj RT 50.4 Gy/28#s January-February 2006; 2006-2009 on Tamx; | All Normal, |

TABLE 10-continued

| Patient history | Serial No of Patients | Age | Stage | Grade | ER/PR/Her2 | MRM/CT/RT | Patient status |
|---|---|---|---|---|---|---|---|
| ER+/PR+ Bad Outcome | 10 | 41, Premeno. | ILC, R Br | T2N0M0 | P/P | Switched to Aromasin in February 2009; Last F/up April 2011 all Normal. April 2003 c/o Lump R Br(6 mths), H/o Hypothyroid, Trucut Biopsy, April 2003 MRM, Bone scan-N, April-June 2003 CT-AC x6; RT; September 2007 local recurrence R ch. wall & Wide exi of R chest wall lesion, CT-FECx6 November 2007-February 2008; March 2008 No hormonal Rx past 4 yrs, Adv Anastrozole; Not been taking Anastrozole; F/up 05 2010 R&L br N & on Anastrazole now; May 2011 Br N, U/S N continue Anastrazole; all Normal; September 2011 Cardio checkup-N, pain in L neck, No node identified clinically, Sonography, TSH, FT4-All N, Adv. see Endocrinologist for Thyroxene replacement | Mets and alive; Local recurrence within 4 yrs, defaulted on CT |
| ER+/PR+ Bad Outcome | 11 | 54, Post | IDC-3, R Br | T2N0M0 | P/P | H/O Hypothyroid, vomitting atleast 1/day for 15 days(March 2001), c/o Thyrotoxicosis in Gastritis; MRM (R Br) June 2004, Post op. Green color urine, No fam history; CT-FACx6 (July-October 2004); C/o Seizures, Brain CT, given anticonvulsants June 2008, RT June 2008, completed Palli WBRT 30Gy/10# 2 weeks; 2x CT-Gem + Cis (11 & 30/07/08); Br Ca (Stage 4) + Intracranial Mets, on Hormonal therapy, refused treatment; completes Palli RT & CT-Gem + Cis 29/08/08; altered sensorium, fever, vomit, bluish color of arm, 2units of FFP + 2 red blood transfusion, discharged for Palli care at home 18/09/08 | Diag./MRM June 2004, Bone & Brain Mets, expired in 4 yrs September 2008 |
| | 12 | 43, Post | ILC, R Br | T2N2M0 | P/P | April 2004: Lump in Br; May 2004: MRM: May-September 2004: CT-FAC x6 September-November 2004: RT 50.4Gy/18#; September 2004: Started Tamx; February 2005: came back w pain, on Novoldex; October 2005 Bone scan-multiple mets adv RT; June 2006: Bone, liver, lung mets; March 2007: CT-Gem + Cis x6; June 2007: RT 30Gy/10#; September 2007: Intracranial CT-Methotrexate; September 2007: Expired | Expired in 3.5 yrs. Bone, lung, live mets within 1-2 yrs |
| | 13 | 58, Post | ILC; L Br | — | P/80% P | Febnary 2002 c/o severe back pain, Op. Laminectomy, surg. D9 vertebra, found Br mass; Trucut Biopsy for Br, Diag. | Mets and dead; Came w bone mets, possible |

TABLE 10-continued

| Patient history | Serial No of Patients | Age | Stage | Grade | ER/PR/Her2 | MRM/CT/RT | Patient status |
|---|---|---|---|---|---|---|---|
| | | | | | | ILC w multiple bone mets, recd RT for spinal lesions, pan-CK +ive; February 2002 CT-Dexona; June 2006 On Letrozole, c/o pain in R shoulder, lower back ache, recd. Palli RT 20Gy/5#/1 wk | met recurrence within 4 years? |
| ER+/PR+ Bad Outcome | 14 | 66 | IDC-3; R Br | T2N1M0 (L Br) | 80% P/N/100% P | H/o Hystrectomy(87), Ht, Hypothyroid; February 2003: Lump, MRM + BCS, RT; April-September 2003 On Herceptin & Xeloda, locally recurrent T nodules ++ all over reconstructed Br; June 2003 Nodules regressed, RT; October 2003 L Br-N, skin healthy 3 weekly dose of Herceptin; December 2003 R Br noticed, FNAC +ve; January 2004 Local recurrence, recd. FAC, Tamx, Letrozole, started on Palli Gemcitabine; February 2004 C/o Met AdenoCa advanced disease, recd. Palli CT ×6, planned CT-5FU + Levoflex/weekly; April 2004 Palli Mast (R); September 2004 only on supportive care, c/o severe pain in neck & chest wall, unconciousness, giddiness due to locally recurrent disease, adv. Brain CT | Mets and dead; Progressive disease despite CT, RT, Hormonal therapy, local recurrence in <1 yr |
| | 15 | 61 | IDC-3; R Br | pT3N2aMx | P/5% P/P | R Br TCB in September 2003; R MRM September 2003; CT-FECx3 September 2003-November 2003; RT 50.4Gy November 2003-January 2004; CT-FECx3 November 2003-January 2004; Normal F/U May 2004; Ricurred in L Br 2007; L-MRM 2007; aggressive disease as −/+; Bone mets in March 2009; Now metastatic progressive disease; Likely expired as per Dr Patil since metastatic dis in 2009 | Recurred in 3 yrs to L br and to bone in 5 yrs; Likely expired. |
| | 16 | 48 | IDC3; L Br | T2N2aM0 | P/P/N | August 2000 L MRM w ax. Clearance; Adj CT-AC×3 IN August-October 2000; Defaulted on CT; Locally advanced dis in 2003; April 2006 Recurrence of IDC of Br in soft tissues of Chest wall; RT 50.4 + 10 Gy/30#s; Defaulted on CT; December 2009 Ch wall recurrence; December 2009 CT-FEC×6 in till April 2010; On Lterozole 2.5 mg × 3 mths; Regular F/up: Last in October 2011 | Alive with recurrent local disease |
| ER+/PR+ Bad Outcome | 17 | 58 | ILC-2A; R Br | pT2N0Mx | P/P/N | Lumpectomy on May 2005; Neo adj CT-FAC×6 June-September 2005; November 2005 Interstitial brachy of R Br ??; February 2006 F/up N | Metastatic disease/Dead |
| | 18 | 55 | IDC-3; L Br | T2N1 | P/P(20%)/N | MRM on February 2005 | Mets and dead |
| ER−/PR− Good Outcome | 19 | 49, Post | IDC-3, L Br, high mitotic case, no embolic or invasion | T2N0M0 | N/N | Lumpectomy on March 2003, have lumpectomy sample, MRM April 2003 | Alive, 9 yrs since MRM |

TABLE 10-continued

| Patient history | Serial No of Patients | Age | Stage | Grade | ER/PR/Her2 | MRM/CT/RT | Patient status |
|---|---|---|---|---|---|---|---|
| | 20 | 62, Post | IDC-3, L Br but necrosis present | T4N0Mx | N/N | Mammo, Trucut (01/01/04), Lump, MRM (L Br) 6 & 7/01/04; CT-FAC×6 (17/01-10/05/04), RT 50.4Gy/28# (02/06-08/07/04); August 2006-In remission; August 2007 - c/o UTI, vomitting, fever, adv CT scan, Mammo; October 2007 - Inj Avastin; April 2008 - R-Br Normal; July 2009 - lower back pain, bone scan-no Met; January 2012 - 8 yrs since MRM, now pain in R Br, adv Mammo | 8 yr since MRM (L Br), currently c/o pain in R Br |
| | 21 | 49, Premeno. | IDC, R Br | T2N2M0 | N/N | August 2003: Lump R Br(1.5 mths), MRM; September-December 2003 CT-FEC x6; October 2003 RT 50.4GY/26# Febrnary 2006: All Normal; November 2006: Accident, Rt shoulder bruise | Alive & no mets |
| ER−/PR− Good Outcome | 22 | 61, | IDC-3 w DCIS foci; R Br | pT2N1Mx | N/N | October 2008 F/u L Br, R MRM-N | No mets and alive |
| | 23 | 51, Premeno. | IDC-3, R Br | T2N1M0, pT3N2M0 | N/N/N | 91, '00: FNAC for Lump L, R Br-Neg(repectively); H/o Tubectomy; August 2003: c/o Lump in Br(2 yrs), pain only during menstural cycle, MRM (R); August 2003-January 2004 CT-FEC x6; December 2003 RT; April 2004 Recurrent Br Ca Nodule-exi biopsy; June 2008 5 yrs since MRM, All Normal; June 2009: Bone scan-Normal; June 2011: Multiple neck nodules-Met Ca; July 2011: Local RT, start Capecitabine, September 2011: CT, 1 week break then start Capecitabine; December 2011: 5 cycles of Capecitabine; January 2012: —? | Alive with Mets; 1st FNAC done in '91, then '00, MRM in 03, local recurrence in 1 yr, mets in 8 yrs |
| | 24 | 43 | IDC-3 + DCIS, L Br | T2N1M0 | N/N | L-MRM Febrnary 2003: Adj CT-AC×4 March-May 2003; Adj RT 50.4Gy/28 # + Boost RT 14Gy/7# in July 2003; CT-Pacli×4 August-September 2003; Liver mets August 2008; Alive with mets | Alive with mets CHECK |
| | 25 | 47 | IDC-3 | pT2N0M0 | N/N/P | June 2001 L Br surgery & B/L oophorectomy: Adj CT-EC×4 July-September 2001; Adj RT 50.4 + 10 Gy/33#s October 2001; On Tamx 2002-2004 & all F/up normal. | Alive with local mets |
| | 26 | 57 | IDC; Medullary Ca; R Br | T2N0M0; Stg 2A | N/N/N | R-MRM February 2006: Adj CT-AC×4 IN March-May 2006; Adj CT-Paclix 12 May-August 2006; Adj RT to R ch wall 50.4Gy/28# August-October 2006; On regular F/up in 2007-2009, all normal, minor c/o swelling in arms w pains; May 2010 local recurrence to L breast; | Doing well |

TABLE 10-continued

| Patient history | Serial No of Patients | Age | Stage | Grade | ER/PR/Her2 | MRM/CT/RT | Patient status |
|---|---|---|---|---|---|---|---|
| ER−/PR− Good Outcome | 27 | 35 | IDC-III; L Br | T2N1M0; Stg 2B | N/N/P | Had L BC Surgery January 2006: Adj CT-TACx6 in February-May 2006: Adj CT Pacli + Herceptin x12 in May-August 2006; | Doing well |
| ER−/PR− Bad Outcome | 28 | 68, Post | IDC-3, R Br | T3N1M0 | N/N | June 2003: Lump in R Br(3 wks), MRM, Bone scan-possible skeletal mets; June 2003-January 2004: CT-AC x6; June 2004 No c/o Mets, Facial (R) Palsy, severe weakness, no other Neuro complaints; October 2004 severe pain L shoulder, Bone scan-multiple skeletal mets, adv. Palli CT-Taxane and RT | Mets and dead; Bone mets within 1 year |
|  | 29 | 50 | R Br | T4bN1M1 | — | June 2000: Diag Br Ca w pulmonary met in Hyd, January-April 2003 Palli CT-FAC; April 2003: R Br-mass reduced in size; November 2003 c/o vomit, headache, disorientation −> Brain mets, given Palli RT | Brain mets in 3 yrs; dead |
|  | 30 | 42, Premeno. | IDC-3, R Br | T2N1M0 | N/N | MRM August 2003, adj CT-FEC x1/FEC x6; RT taken; June 2005 H/0 headache, Recurred in 22 months in brain, crainiotomy done June 2005 | Barin mets in 1.8 yrs yrs of MRM; Dead |
|  | 31 | 55, Post | IDC-2, R Br | T4N2M0 | N/N/P | Neo CT-AC x1/RT + Tamoxifen x4/ MRM-3c/Her2+ & Xeloda x1; Met: L Br; Bones in 10 months/CT-Herpceptin + Vinorelbrine | Mets and dead: L Br Bones in 10 months |
|  | 32 | 38, Premeno. | ILC + IDC-3 + DCIS; L Br |  | N/N | February 2003 FNAC, Lump, MRM: February-August 2003 CT-AC x6; March 2003 RT 50.4GY/28#; February 2004 - All Normal; July 2005 vomitting, headache, L facial pain, adv Dexona, Hydrocort; October 2005 feels weak, mild pallor, Bone marrow asp & Bx-met Ca, adv CT-Docetaxel/week; June 2006 FNAC R Br-IDC, tiny brain mets, bone marrow-met Ca, started on Xeloda; July 2006 severe headache(1 mth), FNAC R Br(swelling) +ve, Mets in contralateral Br, bone marrow, brain, Carcinomatous meningitis. Adv contuinue CT, Palli RT spinal, cranial, femur; December 2006 Bone scan-some lesions regressed, some increased. | Mets and dead; Bone (3 yrs) and subsequently brain mets (4 yrs) |
| ER−/PR− Bad Outcome | 33 | 45, Premeno. | IDC-3 w DCIS foci, L Br | T3N1Mx, pT3N2aM0 (Stage-3a) | N/N | c/o Br lump-6 mths, H/o Hashiinoto's Thyroiditis, Thyromegaly(2 yrs); July 2003: MRM; July-December 2003: CT-FEC x6; September 2003: RT 50.4 Gy/28# given after 3rd CT; November 2003: cold, anemia w Mycoplasma infection, given washed RBC; Sep. 03, 2005: c/o Rt Hemiparesis(1 week), loss of appetite & weakness, Bone, brain, chest scan show mets. Adv Palli RT; Nov. 03, 2005: Expired, COD: Multiple brain sec., Pri Br Ca w Liver mets | Mets and dead; Expired within 2 yrs with Brain, liver mets |

TABLE 10-continued

| Patient history | Serial No of Patients | Age | Stage | Grade | ER/PR/Her2 | MRM/CT/RT | Patient status |
|---|---|---|---|---|---|---|---|
| | 34 | 62 | IDC-3, R Br | T3N1Mx; Stg 4 | N/N/P | Br lump since 2003; June 2006 lung mets; Neoadj CT-TACx4 in October 2006; T increased in size, CT changed to Gem + Cisplatin x March 2007; on Xeloda since July 2007; T increased in size; Start Capcitabine/Vincristine/Gem + irinotecan by July 2008 -> Palliative R MRM July 2008; Lung mets; cough & itching in May 2009 advised Xeloda + Tykerb; October 2009 endoxan, celecoxib; July 2010 disease progression to LN mets + cough | Had multiple regimes of CT, Mets and dead |
| ER−/PR− Bad Outcome | 35 | 60 | IDC-3b, | T4N2M1; IV | TBD | June 2004 came w lump in R br + bone & brain mets; Neo-adj CT-Doce + epirubicin x3 June-August 2004; Progressive disease thus changed to salvage CT Gemcitabine + Vinorelbine August 2004; T mass increased, CT changed to palliative CT-TACx4 January-March 2005; Had HT also, Patient passed away on 17.8.2005 | Multiple CTs; Metastatic adenocarcinoma, dead |
| | 36 | 44 | IDC-3; R Br | TxN1M1 | N/N/P2+ | B/L Lump excision in August 2005; R-MRM on November 2005; Adj CT-FECx6 November 2005-February 2006; RT 50.4/28# March-May 2006; December 2006 brain mets & crainiotectomy done; January 2007 RT to brain 45Gy/25#s; February 2007 c/o cough B/L lung mets; Not willing for injectible CT hence oral CT advised | Mets and dead |

I claim:

1. A combination of
biological markers consisting of CD44, ABCC4, P-cadherin and β-catenine
for prognosis of breast cancer or recurrence of breast cancer, based on the estrogen receptor and progesterone receptor status.

2. The combination of claim 1, wherein the markers are located on breast cancer cells of a subject at locations selected from a group comprising cell membrane, cytoplasm, nucleus, and nuclear membrane or any combination thereof.

3. The combination of claim 1, further comprising one or more biological markers ABCG2, CD133, and/or Oct-4.

* * * * *